United States Patent [19]

Melchers

[11] Patent Number: 5,981,184

[45] Date of Patent: Nov. 9, 1999

[54] SCREENING KIT AND PROCESS FOR DETERMINING ACTION OF SUBSTANCES INHIBITING THE P-TYPE ATPASE ACTIVITY OF *HELICOBACTER PYLORI*

[75] Inventor: Klaus Melchers, Aach, Germany

[73] Assignee: Byk Gulden Lomberg Chemische Fabrik GmbH, Constance, Germany

[21] Appl. No.: 08/849,480

[22] PCT Filed: Nov. 30, 1995

[86] PCT No.: PCT/EP95/04711

§ 371 Date: Jun. 2, 1997

§ 102(e) Date: Jun. 2, 1997

[87] PCT Pub. No.: WO96/17066

PCT Pub. Date: Jun. 6, 1996

[30] Foreign Application Priority Data

Dec. 2, 1994 [DE] Germany .............................. 44 42 970
Feb. 18, 1995 [DE] Germany ........................... 195 05 645

[51] Int. Cl.$^6$ .............................. C12Q 1/68; C12N 15/55; C12N 15/63
[52] U.S. Cl. .............................. 435/6; 435/18; 435/320.1; 435/252.3; 435/252.33; 435/7.32; 435/7.37; 536/23.2; 536/23.7
[58] Field of Search ................................. 536/23.2, 23.7; 435/6, 18, 320.1, 252.3, 252.33, 7.32, 7.37

[56] References Cited

FOREIGN PATENT DOCUMENTS

94/04161  3/1994  WIPO .
94/23059  10/1994  WIPO .

OTHER PUBLICATIONS

Ge et al. "Nucleotide sequence and mutational analysis indicate that two *Helicobacter pylori* genes encode a P–type ATPase and a cation–binding protein associated with copper transport". Mol. Microbiol. 15 (1): 97–106, Jan. 1995.

Harman et al. "Characterization of a P–type ATPase of *Helicobacter pylori*." Am. J. Gastroenterology 89(8): 1288, Aug. 1994.

Stokes et al. "Structures of P–type and F–type ion pumps." Curr. Opin. Struct. Biol. 4(2):197–203, 1994.

Lutsenko et al. " Organization of P–Type ATPases: Significance of Structural Diversity". Biochemistry 34(48):15607–15613, Dec. 5, 1995.

Pesci et al. Genetic, enzymatic, and pathogenic studies of the iron superoxide dismutase of *Camoylobacter jejuni*. Infection & Immunity 62(7): 2687–2694, Jul. 1994.

Chemical Abstracts, 119 (1993); Beil et al., *Pharmacology* 1993, 47(2), 135–140.

*Primary Examiner*—Robert A. Wax
*Assistant Examiner*—Gabriele Bugaisky
*Attorney, Agent, or Firm*—Jacobson, Price, Holman & Stern, PLLC

[57] ABSTRACT

A screening-model is disclosed for determining the inhibiting effect of substances on the P-type ATP-ase activity of Helicobacter. The screening model in question comprises: (a) a recombinant organism consisting of host cells transformed with at least one P-type ATP-ase gene which can be controlled via a promoter; (b) an inductor for gene activation of the P-type ATP-ase; (c) cations which inhibit the metabolic activity of the recombinant organism only in the presence of Helicobacter P-type ATP-ase; and (d) a measurement device for determining the metabolic activity of the recombinant organism.

26 Claims, 24 Drawing Sheets

FIG. 2a

```
CTCGAGATCA  AACCCAATCC  TAACATTTTC  CCCATGCTTT  TAGACATTGC   50
CATCAAACAC  CCCCATGCTA  AAGTCATTGC  GCCTAAGGCT  AATTGAAGAGC  100
TTTTTTCGCT  CATCCCTAAT  TTGCAATGCT  TTTTTGTGGA  GCATTTTAAA   150
GAAGCGTTAG  AAATCTTACA  AAACCCTGAA  ATCAAAGCAG  ACACCCACAC   200
GAAAAAACTA  CCCTTTAAAA  CGATAGAATT  GAACGATAAA  GAGTATTATT   250
TTTCAGACGC  CTATGCATTA  GATTTTAAAG  AAGTTAAGGG  GCAAGCTGTC   300
GCTAAAGAAG  CCGCTTTGAT  CGCTAGCGCT  GGGTTTCATA  ACTTGATTTT   350
AGAGGGAAGT  CCAGGGTGTG  GGAAAAGCAT  GATCATTAAT  CGCATGCGTT   400
ATATTTTACC  TCCCTTAAGC  CTGAATGAAA  TCCTAGAAGC  GACAAAATTA   450
CGCATTTTAA  GCGAACAAGA  CAGCGCCTAT  TACCCCTTAA  GGAGTTTTAG   500
AAACCCTCAC  CAAAGCGCTT  CAAAATCCAG  CATTTTAGGC  TCAAGCTCTC   550
TAAAAGAGCC  AAAACCCGGC  GAAATCGCCG  TAGCGCATAA  CGGCATGCTT   600
TTTTTTGATG  AATTGCCTCA  TTTTAAAAAG  GAAATTTTGG  AAGCTTTAAG   650
AGAGCCTTTA  GAAAACAATA  AATTGGTGGT  TTCACGAGTG  CATAGCAAAA   700
TTGAATACGA  AACCTCTTTT  TTATTTGTGG  GGGCTCAAAA  CCCTTGCTTG   750
TGTGGGAATT  TACTCAGTGC  GACCAAAGCA  TGCCGTTGCC  AAGACAGAGA   800
AATCACGCAG  TATAAAAACC  GCTTGAGCGA  GCCTTTTTTA  GATAGGATTG   850
ATTTGTTTGT  GCAAATGGAA  GAGGGGAATT  ATAAAGACAC  GCCGTCGCAT   900
```

FIG. 2b

```
                                                                    950
TCTTGGACTT  CAAAAGAGAT  GCATCAATTA  GTATTATTAG  CTTTCAAACA
                                                                   1000
GCAAAAATTA  AGGAAACAGA  GCGTTTTTAA  TGGTAAGCTT  AATGAAGAGC
                                                                   1050
AGATAGAACG  ATTTTGCCCT  TTAAACGCTG  AAGCAAAAAA  GTTGTTAGAG
                                                                   1100
CAGGCGGTTG  AAAGGTTTAA  TCTGTCCATG  CGCTCTGTTA  ATAAGGTCAA
                                                                   1150
AAAGGTCGCC  AGGACGATTG  CGGATTTAAA  CGCTTGCGAG  AATATAGAAA
                                                                   1200
AATCTCACAT  GCTTAAAGCG  CTGAGTTTTA  GAAAGATTTC  TTAAAAGGAT
                        1218
TTTTATAAGG  GAGAGAAA
```

```
1219
ATG CAA GAA TAC CAC ATT CAT AAT TTG GAT TGC CCT GAT TGC GCG
Met GlN Glu Tyr His Ile His AsN Leu Asp Cys Pro Asp Cys Ala
                                10
TCT AAA TGG GAA AGG GAT TTA AAC AAA CTA GAC TAT GTG AAA AAA
Ser Lys Leu Glu Arg Asp Leu AsN Lys Leu Asp Tyr Val Lys Lys
                    20                                        30
GCT CAA ATC AAT TTC AGC ACC AGC AGG TTG TTT TTG GAC ACG AGC
Ala GlN Ile AsN Phe Ser Thr Ser Arg Leu Phe Leu Asp Thr Ser
                                    40
GAT TTT GAA AAA GTT AAG GCT TTT ATC AAG CAG AAT GAA CCG CAT
Asp Phe Glu Lys Val Lys Ala Phe Ile Lys GlN AsN Glu Pro His
                        50                                    60
TTG AGC CTG TCT TTT AAA GAG GCC GCA GAA AAG CCC TTG AGT TTT
Leu Ser Leu Ser Phe Lys Glu Ala Ala Glu Lys Pro Leu Ser Phe
                                    70
ACG CCA CTC ATT GTT ACG ATC GCT GTC TTT TTA GGC GCG ATT TTA
Thr Pro Leu Ile Val Thr Ile Ala Val Phe Leu Gly Ala Ile Leu
                        80                                    90
ATC TTA CAC CTA AAC CCT AGC CCT TTG ATT GAA AAG GCT ATG TTT
Ile Leu His Leu AsN Pro Ser Pro Leu Ile Glu Lys Ala Met Phe
                                    100
TTC GTG TTG GCT TTG GTG TAT CTA GTG AGC GGT AAA GAT GTG ATT
Phe Val Leu Ala Leu Val Tyr Leu Val Ser Gly Lys Asp Val Ile
                        110
TTA GGG GCG TTT CGT GGG CTT AGG AAA GGG CAG TTT TTT GAT GAA
Leu Gly Ala Phe Arg Gly Leu Arg Lys Gly GlN Phe Phe Asp Glu
                                    130
```

FIG. 2c

| | | | | | | | | | | | | | |
|---|---|---|---|---|---|---|---|---|---|---|---|---|---|
| AAC | GCT | TTG | ATG | CTC | ATT | GCG | ACT | ATT | GCG | GCT | TTT | TGC | GTG | GGG |
| AsN | Ala | Leu | Met | Leu<br>140 | Ile | Ala | Thr | Ile | Ala | Ala | Phe | Cys | Val | Gly<br>150 |
| GCT | TAT | GAA | GAG | AGC | GTG | TCT | ATT | ATG | GTG | TTT | TAT | TCA | GCG | GGC |
| Ala | Tyr | Glu | Glu | Ser<br>20 | Val | Ser | Ile | Met | Val<br>160 | Phe | Tyr | Ser | Ala | Gly |
| GAA | TTT | TTG | CAA | AAA | CTC | GCT | ATC | GCT | CGC | TCT | AAA | AAA | TCC | CTT |
| Glu | Phe | Leu | GIN | Lys<br>170 | Leu | Ala | Ile | Ala | Arg | Ser | Lys | Lys | Ser | Leu<br>180 |
| AAG | GCT | TTA | GTG | GAT | GTC | GCT | CCT | AAT | TTG | GCT | TAT | TTG | AAA | AAG |
| Lys | Ala | Leu | Val | Asp | Val | Ala | Pro | AsN | Leu<br>190 | Ala | Tyr | Leu | Lys | Lys |
| GGC | GAT | GCG | TTA | GTG | AGC | GTT | GCG | CCT | GAA | GAT | TTA | AGA | ATT | AAT |
| Gly | Asp | Ala | Leu | Val<br>200 | Ser | Val | Ala | Pro | Glu | Asp | Leu | Arg | Ile | AsN<br>210 |
| GAC | ATT | GTG | GTG | GTG | AAA | GTC | GGC | GAA | AAA | GTG | CCT | GTG | GAT | GGC |
| Asp | Ile | Val | Val | Val | Lys | Val | Gly | Glu | Lys<br>220 | Val | Pro | Val | Asp | Gly |
| GTG | GTG | ATT | AAG | GGC | GAA | AGT | TTG | CTA | GAT | GAA | AGG | GCG | TTG | AGC |
| Val | Val | Ile | Lys | Gly<br>230 | Glu | Ser | Leu | Leu | Asp | Glu | Arg | Ala | Leu | Ser<br>240 |
| GGG | GAG | TCT | ATG | CCG | GTT | AAT | GTC | AGC | GAA | CGC | TCT | AAA | GTT | TTA |
| Gly | Glu | Ser | Met | Pro | Val | AsN | Val | Ser | Glu<br>250 | Arg | Ser | Lys | Val | Leu |
| GGG | GGG | AGC | TTG | AAT | TTA | AAA | GCG | GTC | CTT | GAA | ATT | CAA | GTA | GAG |
| Gly | Gly | Ser | Leu | AsN<br>260 | Leu | Lys | Ala | Val | Leu | Glu | Ile | GIN | Val | Glu<br>270 |
| AAA | ATG | TAT | AAA | GAT | TCT | TCT | ATC | GCT | AAA | GTG | GTA | GAT | TTG | GTC |
| Lys | Met | Tyr | Lys | Asp | Ser | Ser | Ile | Ala | Lys<br>280 | Val | Val | Asp | Leu | Val |
| CAA | CAA | GCC | ACG | AAT | GAA | AAG | AGC | GAA | ACC | GAG | AAA | TTT | ATC | ACT |
| GIN | GIN | Ala | Thr | AsN<br>290 | Glu | Lys | Ser | Glu | Thr | Glu | Lys | Phe | Ile | Thr<br>300 |
| AAA | TTT | TCA | CGC | TAC | TAC | ACC | CCA | AGC | GTT | TTA | TTC | ATT | GCG | TTA |
| Lys | Phe | Ser | Arg | Tyr | Tyr | Thr | Pro | Ser | Val<br>310 | Leu | Phe | Ile | Ala | Leu |
| ATG | ATT | GCT | GTA | TTA | CCG | CCC | TTA | TTT | TCT | ATG | GGG | AGC | TTT | GAT |
| Met | Ile | Ala | Val | Leu<br>320 | Pro | Pro | Leu | Phe | Ser | Met | Gly | Ser | Phe | Asp<br>330 |
| GAG | TGG | ATT | TAT | AGG | GGG | CTT | GTG | GCT | TTA | ATG | GTG | AGC | TGC | CCT |
| Glu | Trp | Ile | Tyr | Arg | Gly | Leu | Val | Ala | Leu<br>340 | Met | Val | Ser | Cys | Pro |

FIG. 2d

```
TGC GCG TTA GTG ATT TCT GTG CCT TTA GGG TAT TTT GGA GGC GTG
Cys Ala Leu Val Ile Ser Val Pro Leu Gly Tyr Phe Gly Gly Val
            350                                         360
GGA GCG GCG AGC CGA AAG GGT ATT TTA ATG AAA GGC GTG CAT GTT
Gly Ala Ala Ser Arg Lys Gly Ile Leu Met Lys Gly Val His Val
                20                      370
TTA GAA GTG CTT ACC CAA GCT AAA AGC ATC GCC TTT GAT AAA ACC
Leu Glu Val Leu Thr Gln Ala Lys Ser Ile Ala Phe Asp Lys Thr
                380                                     390
GGC ACT TTG ACT AAA GGC GTT TTT AAA GTA ACA GAT ATT GTC CCG
Gly Thr Leu Thr Lys Gly Val Phe Lys Val Thr Asp Ile Val Pro
                                    400
CAA AAC GGG CAT TCT AAA GAA GAA GTT TTG CAT TAC GCT TCT TGT
Gln Asn Gly His Ser Lys Glu Glu Val Leu His Tyr Ala Ser Cys
            410                                         420
TCG CAG CTC TTG TCC ACG CAC CCT ATC GCT TTA TCC ATT CAA GAA
Ser Gln Leu Leu Ser Thr His Pro Ile Ala Leu Ser Ile Gln Glu
                                430
GCA TGC GAA GAA ATG TTA AAG GAC GAC AAG CAC CAG CAT GAC ATT
Ala Cys Glu Glu Met Leu Lys Asp Asp Lys His Gln His Asp Ile
                440                                     450
AAA AAT TAC GAA GAA TTG AGC GGA ATG GGG GTT AAA GCG CAA TGC
Lys Asn Tyr Glu Glu Leu Ser Gly Met Gly Val Lys Ala Gln Cys
                                460
CAT ACG GAT TTA ATC ATC GCA GGG AAT GAA AAA ATG CTG GAT CAA
His Thr Asp Leu Ile Ile Ala Gly Asn Glu Lys Met Leu Asp Gln
            470                                         480
TTC CAT ATC GCG CAC AGC CCT TCC AAA GAA AAC GGC ACG ATC GTG
Phe His Ile Ala His Ser Pro Ser Lys Glu Asn Gly Thr Ile Val
                                490
CAT GTG GCT TTC AAC CAA ACT TAT ATA GGC TAT ATC GTC ATT AGC
His Val Ala Phe Asn Gln Thr Tyr Ile Gly Tyr Ile Val Ile Ser
            500                                         510
GAT GAG ATT AAA GAT GAC GCC ATA GAG TGC TTA AGG GAT TTA AAA
Asp Glu Ile Lys Asp Asp Ala Ile Glu Cys Leu Arg Asp Leu Lys
                                520
GCG CAA GGG ATA GAA AAT TTT TGC ATT TTG ATG GGG GAC AGA AAA
Ala Gln Gly Ile Glu Asn Phe Cys Ile Leu Met Gly Asp Arg Lys
            530                                         540
AGC GCG ACT GAG AGC ATC GCT CAA ACT CTG GGC TGT GAA TAT TAT
Ser Ala Thr Glu Ser Ile Ala Gln Thr Leu Gly Cys Glu Tyr Tyr
                                550
```

FIG. 2e

```
GCG AGT TTG TTG CCT GAA GAA AAA ACG AGC GTG TTT AAA ACT TTT
Ala Ser Leu Leu Pro Glu Glu Lys Thr Ser Val Phe Lys Thr Phe
            560                                         570
AAA GAA CGC TAT AAA GCC CCG GCG ATT TTT GTA GGC GAT GGT ATC
Lys Glu Arg Tyr Lys Ala Pro Ala Ile Phe Val Gly Asp Gly Ile
                                    580
AAT GAC GCT CCG ACT CTA GCG AGC GCT GAT GTG GGG ATT GGC ATG
AsN Asp Ala Pro Thr Leu Ala Ser Ala Asp Val Gly Ile Gly Met
                590                                     600
GGG AAA GGC TCA GAA TTG AGC AAG CAA AGC GCG GAC ATT GTG ATC
Gly Lys Gly Ser Glu Leu Ser Lys GIN Ser Ala Asp Ile Val Ile
                                610
ACC AAT GAC TCC TTA AAT TCG TTA GTG AAA GTT TTA GCG ATC GCT
Thr AsN Asp Ser Leu AsN Ser Leu Val Lys Val Leu Ala Ile Ala
            620                                         630
AAA AAA ACT AAA AGC ATT ATT TGG CAA AAT ATC TTG TTC GCT TTG
Lys Lys Thr Lys Ser Ile Ile Trp GIN AsN Ile Leu Phe Ala Leu
                                640
GGG ATT AAA GCC GTT TTT ATC GTG CTA GGG CTT ATG GGG GTA GCG
Gly Ile Lys Ala Val Phe Ile Val Leu Gly Leu Met Gly Val Ala
            650                                         660
AGC TTG TGG GAA GCG GTC TTT GGC GAT GTG GGG GTT ACG CTT TTA
Ser Leu Trp Glu Ala Val Phe Gly Asp Val Gly Val Thr Leu Leu
                                    670    3279
GCC TTA GCC AAC TCC ATG CGC GCA ATG AGA GCT TAA
Ala Leu Ala AsN Ser Met Arg Ala Met Arg Ala ***
            680                             686
                    3301                            3331
         AG CCTTGAATCC ATCATCAAAG AGCTAGAAGG GGGGCAAAAT GAACCACATA
                                                    3381
         GAAAAACTAC TCCAAACCTT AGCGCCTAAA GGGGTGGAGT TTAGGAAGTT
                                3411
         GGGGGAGGTG CTAGAATATG ATCTGAATTC
```

FIG. 3a

TRANSLATION OF A NUCLEIC ACID SEQUENCE

DNA sequence PRH514.
Total number of bases is: 3097.
Analysis done on the complete sequence.
Done on (absolute) phase(s): 1, 2 and 3.
Using the Universal genetic code.

ORF Analysis

| #     | Start | End  | Frame |
|-------|-------|------|-------|
| ORF 1 | 115   | 1632 | 1     |

FIG. 3b

```
         10         20         30         40         50         60         70         80         90        100
GATCGATCATCTCAATGGCGTGTTATTCGTGGATAAATTATCCATTTTGAAGGCTAAGAATTATCCATTTTGAAAAGAATTAAGAATTAAGTAAAAATCCAGA 110        120        130        140        150        160        170        180        190        200
AACAAGTCTTAATCATGATTAACACGATATATTTGCGCGACCATGCAAAGGGGAGTGGCAGAAATCGTGGCTGTAGAAGCGACTTTCACAAGGGCTTTGCC
          M  I  N  T  I  F  C  A  T  M  Q  R  G  V  A  E  I  V  A  V  E  A  T  F  T  R  A  L  P 210        220        230        240        250        260        270        280        290        300
GGCGTTTGTGATTTCAGGCTTGGCTAATAGCTCTATCCAAGAAGCCAAACAGCGGGTCCAATCGGCTTACAAAATAACGATTTCACTTTCCCGCCCTTA
 A  F  V  I  S  G  L  A  N  S  S  I  Q  E  A  K  Q  R  V  Q  S  A  L  Q  N  N  D  F  T  F  P  P  L 310        320        330        340        350        360        370        380        390        400
AAAATCACCATCAACCTTCCCCTTCAGATTGCCTAAATCCGGGAGCCATTTGATTGCCTATCGCTCTTTAATCGCTTGCAAAACAAGAGTTGG
 K  I  T  I  N  L  S  P  S  D  L  P  K  S  G  S  H  F  D  L  P  I  A  L  L  I  A  L  Q  K  Q  E  L 410        420        430        440        450        460        470        480        490        500
CTTTTAAAGAGTGGTTGCTTTGGGGAGTTAGGGCTTGATGGCAAGATCAAACCCATGCAAATCCTAACATTTCCCCATGCTTTAGACATTGCCATCAAACA
 A  F  K  E  W  F  A  F  G  E  L  G  L  D  G  K  I  K  P  N  P  N  I  F  P  M  L  L  D  I  A  I  K  H
```

FIG. 3c

```
510        520        530        540        550        560        570        580        590        600
 |          |          |          |          |          |          |          |          |          |
CCCCATGCTAAAGTCATTGCGCCTAAGGCTAATGAAGAGCTTTTTCGCTCATCCCTAATTGCAATGCTTTTTGTGGAGCATTTAAAGAAGCGTA
 P  H  A  K  V  I  A  P  K  A  N  E  E  L  F  S  L  I  P  N  L  Q  C  F  F  V  E  H  F  K  E  A  L 610        620        630        640        650        660        670        680        690        700
 |          |          |          |          |          |          |          |          |          |
GAAATCTTACAAAACCCTGAAATCAAAGCAGACACCCACAGAAAAACTACCCTTAAAACGATAGAATTGAACGATAAAGAGTATATTTTCAGACG
 E  I  L  Q  N  P  E  I  K  A  D  T  H  T  K  K  L  P  F  K  T  I  E  L  N  D  K  E  Y  Y  F  S  D 710        720        730        740        750        760        770        780        790        800
 |          |          |          |          |          |          |          |          |          |
CCTATGCATTAGATTTTAAAGAAGTTAAGGGGCAAGCTGTCGCTAAAGAAGCCGTTGATCGCTAGCGCTTGGTTCATAACTGATTTTAGAGGGAAG
 A  Y  A  L  D  F  K  E  V  K  G  Q  A  V  A  K  E  A  A  L  I  A  S  A  G  F  H  N  L  I  L  E  G  S 810        820        830        840        850        860        870        880        890        900
 |          |          |          |          |          |          |          |          |          |
TCCAGGGTGTGGGAAAAGCATGATCATTAATCGCATGCGTTATATTTACCTCCCTTAAGCCTGAATGAAATCCTAGAAGGCACAAAATTACGCATTTA
 P  G  C  G  K  S  M  I  I  N  R  M  R  Y  I  L  P  P  L  S  N  E  I  L  E  A  T  K  L  R  I  L 910        920        930        940        950        960        970        980        990        1000
 |          |          |          |          |          |          |          |          |          |
AGCGAACAGACAGCGCTATTACCCCCTTAAGGAGTTTTAGAAACCCTCACCAAAGCGCTTCAAATCCAGCATTTAGGCTCAAGCTCTCTAAAGAGC
 S  E  Q  D  S  A  Y  Y  P  L  R  S  F  R  N  P  H  Q  S  A  S  K  S  S  I  L  G  S  S  L  K  E 1010       1020       1030       1040       1050       1060       1070       1080       1090       1100
 |          |          |          |          |          |          |          |          |          |
CAAAACCCGGCGAAATCGCCGCATAACGGCATGCTTTTTTGATGAATTGCCTCATTTAAAAGGAAATTTGGAAGCTTAAGAGACCCTTT
 P  K  P  G  E  I  A  V  A  H  N  G  M  L  F  F  D  E  L  P  H  F  K  K  E  I  L  E  A  L  R  E  P  L
```

FIG. 3d

```
1110        1120        1130        1140        1150        1160        1170        1180        1190        1200
  |           |           |           |           |           |           |           |           |           |
AGAAACAATAAATTGGTGGTTTCACGAGTTGCATAGCAAATTGAATACGAAACCCTCTTTTTATTGTGGGGCTAAACCCTTGCTTGTGTGGAAT
 E  N  N  K  L  V  V  S  R  V  H  S  K  I  E  Y  E  T  S  F  L  F  V  G  A  Q  N  P  L  C  G  N 1210        1220        1230        1240        1250        1260        1270        1280        1290        1300
  |           |           |           |           |           |           |           |           |           |
TTACTCAGTGCGACCAAGCATGCCGTTGCCAAGACAGAGAAATCACGCAGTATAAAAACCGCTTGAGCGAGCCTTTTTAGATAGGATTGATTGTTTG
 L  L  S  A  T  K  A  C  R  C  Q  D  R  E  I  T  Q  Y  K  N  R  L  S  E  P  F  L  D  R  I  D  L  F 1310        1320        1330        1340        1350        1360        1370        1380        1390        1400
  |           |           |           |           |           |           |           |           |           |
TGCAAATGGAAGAGGGAATTATAAAGACACGCCGTCGCATTCTTGGACTTCAAAGAGATGCATCAATTAGTATTATTAGCTTTCAAACAGCAAAAATT
 V  Q  M  E  E  G  N  Y  K  D  T  P  S  H  S  W  T  S  K  E  M  H  Q  L  V  L  L  A  F  K  Q  Q  K  L 1410        1420        1430        1440        1450        1460        1470        1480        1490        1500
  |           |           |           |           |           |           |           |           |           |
AAGGAAACAGAGGCGTTTTAATCTGTCCATGCCTCTGTTAATGAAGCTTAATGAAGAGCAGAACGATATGAAATGAAGCAAAAAGTTGTTAGAGCAGGCGGTT
 R  K  Q  S  V  F  N  G  K  L  N  E  E  Q  I  E  R  F  C  P  L  N  A  E  A  K  K  L  L  E  Q  A  V 1510        1520        1530        1540        1550        1560        1570        1580        1590        1600
  |           |           |           |           |           |           |           |           |           |
GAAAGGTTTAATCTGTCCATGCGCTCTGTTAATAAGGTCAAAAAGGTCGCCAGGACGATTGCGATTTAAACGCTTGCGAGATATAGAAAAATCTCACA
 E  R  F  N  L  S  M  R  S  V  N  K  V  K  K  V  A  R  T  I  A  D  L  N  A  C  E  N  I  E  K  S  H 1610        1620        1630        1640        1650        1660        1670        1680        1690        1700
  |           |           |           |           |           |           |           |           |           |
TGCTTAAAGCGGCTGAGTTTAGAAAGATTTCTTAAAAGGATTTTTATAAGGGAGAGAAATGCAAGAATACCACATTCATAATTTGATTGCCCTGATTG
 M  L  K  A  L  S  F  R  K  I  S  -
```

FIG. 3e

```
1710                1720                1730                1740                1750                1760                1770                1780                1790                1800
  |                   |                   |                   |                   |                   |                   |                   |                   |                   |
CGCGTCTAAATTGGAAAGGGATTAAACAAACTAGATTGAAAAAGCTCAAATCAATTCAGCACCAGCAGGTTGTTTTGGACACGAGCGATTT 1810                1820                1830                1840                1850                1860                1870                1880                1890                1900
  |                   |                   |                   |                   |                   |                   |                   |                   |                   |
GAAAAAGTAAGGCTTTTATCAAGCAGAATGAACCGCATTTGAGCCTGTCTTTAAAGAGGCCCAGAAAAGCCCTTGAGTTTACGCCACTCATTGTTA 1910                1920                1930                1940                1950                1960                1970                1980                1990                2000
  |                   |                   |                   |                   |                   |                   |                   |                   |                   |
CGATCGCTGTCTTTTAGGCGCGATTTAATCTTACACCTAAACCCTAGCCCTTTGATTGAAAAGGCTATGTTTTCGTGTTGGCTTTGGTGTATCTAGT 2010                2020                2030                2040                2050                2060                2070                2080                2090                2100
  |                   |                   |                   |                   |                   |                   |                   |                   |                   |
GAGCGGGTAAAGATGTGATTTTAGGGGCGTTCGTGTGGGCTTAGGAAAGGGCAGTTTTTGATGAAAACGCTTGATCGTCATTGCCGACTATTGCCGCTTT 2110                2120                2130                2140                2150                2160                2170                2180                2190                2200
  |                   |                   |                   |                   |                   |                   |                   |                   |                   |
TGCGTGGGGCTTATGAAGAGAGCGTGTCTATTATGGTGTTTTATTCAGCGGGCGAATTTTGCAAAAACTCGCTATCGCTCGCTCTAAAAATCCCTTA 2210                2220                2230                2240                2250                2260                2270                2280                2290                2300
  |                   |                   |                   |                   |                   |                   |                   |                   |                   |
AGGCTTAGTGGATGTCGCTCCTAATTTGGCTTATTTGAAAAAGGGCGATGCGTTAGTGAGCGTTGCGCCCTGAAGATTAAGAATTAATGACATTGTGGT 2310                2320                2330                2340                2350                2360                2370                2380                2390                2400
  |                   |                   |                   |                   |                   |                   |                   |                   |                   |
GGTGAAAGTCGGGCGAAAAGTGCCCTGTGGTGATTAAGGGCGAAAGTTGCTAGATGAAAGGGCGTTGAGCGGGGAGTCTATGCCGGTTAAT
```

FIG. 3f

```
2410      2420      2430      2440      2450      2460      2470      2480      2490      2500
   |         |         |         |         |         |         |         |         |         |
GTCAGCGAACGCTCTAAAGTTTAGGGGGAGCTTGAATTTAAAAGCGGTCCTTGAATTCAAGTAGAGAAATGTATAAAGATTCTTCTATCGCTAAAG 2510      2520      2530      2540      2550      2560      2570      2580      2590      2600
   |         |         |         |         |         |         |         |         |         |
TGGTAGATTTGGTCCAACAAGCCACGAATGAAAAGAGCGAAACCGAGAAATTATCACTAAATTTCACGCTACTACACCCCAAGCGTTTATTCATTGC 2610      2620      2630      2640      2650      2660      2670      2680      2690      2700
   |         |         |         |         |         |         |         |         |         |
GTTAATGATTGCTGTATTACCGCCCTTATTTCTATGGGAGCTTGATGAGTGGATTTATAGGGGCTTGTGGCTTAATGGTGAGCTGCCCTGCGCG 2710      2720      2730      2740      2750      2760      2770      2780      2790      2800
   |         |         |         |         |         |         |         |         |         |
TTAGTGATTCTGTGCCTTAGGGTATTTGGAGGCGTGGGAGCCGGAGCCGAAAGGTATTTAATGAAAGGCGTGCATGTTTAGAAGTGCTTACCC 2810      2820      2830      2840      2850      2860      2870      2880      2890      2900
   |         |         |         |         |         |         |         |         |         |
AAGCTAAAAGCATCGCCTTTGATAAAACCGGCACTTTGACTAAAGGCGTTTTAAAGTAACAGATATTGTGCCGCAAAACGGGCATTCTAAAGAAGAAGT 2910      2920      2930      2940      2950      2960      2970      2980      2990      3000
   |         |         |         |         |         |         |         |         |         |
TTTGCATTACGCTTCTTGTTCGCAGTCTTATCCACGCACCCTATCGCTTATCCATTCAAGAAGCATGCGAAGAAATGTTAAAGGACGACAAGCACCAG 3010      3020      3030      3040      3050      3060      3070      3080      3090
   |         |         |         |         |         |         |         |         |
CATGACATTAAAAATTACGAAGAATTGAGCGGAATGGGGTTAAAGCGCAATGCCATACGGATTTAATCATCGCAGGAATGAAAAATGCTGGATC
```

FIG. 4a

TRANSLATION OF A NUCLEIC ACID SEQUENCE

DNA sequence PRH948C.
Total number of bases is: 4495.
Analysis done on the complete sequence.
Done by PC/GENE V.6.8 on (absolute) phase(s): 1, 2 and 3.
Using the Universal genetic code.
Underlined: Vector sequences ORF Analysis

| # | Start | End | Frame |
|---|---|---|---|
| ORF 1 | 10 | 936 | 1 |
| ORF 2 | 1162 | 1872 | 1 |
| ORF 3 | 1710 | 1853 | 3 |
| ORF 4 | 1871 | 4094 | 3 |
| ORF 5 | 4098 | 4295 | 3 |
| ORF 6 | 4400 | 4481 | 3 (incomplete at end) |

FIG. 4b

```
        10         20         30         40         50         60         70         80         90        100
        |          |          |          |          |          |          |          |          |          |
TTGAATTCAGATCCGGCCTTAATGCGTCCAGGGCGCTTTGACAGGCAGGTTTAGTGGATAAGCCTGATTTAATGGCAGAGTAGAAATCTTAAAAGTGC
                 D  P  A  L  M  R  P  G  R  F  D  R  Q  V  L  V  D  K  P  D  F  N  G  R  V  E  I  L  K  V 110        120        130        140        150        160        170        180        190        200
        |          |          |          |          |          |          |          |          |          |
ATATTAAAGGCGTGAAACTCGCTAACGATGTGAATTTGCAAGAAGTCGCCAAACTCACCGCAGGGCTTGCAGGGAGCGGATTTAGCAGGAGCCGGATATCATCAATGA
 H  I  K  G  V  K  L  A  N  D  V  N  L  Q  E  V  A  K  L  T  A  G  L  A  G  A  D  L  A  N  I  I  N  E 210        220        230        240        250        260        270        280        290        300
        |          |          |          |          |          |          |          |          |          |
AGCCGGCTTTAGCAGGAAGAAAACCAAAAGAAGTCAGGCAACAGCATTTAAAAGAAGCCGTTGAAAGAGGATTGCGGGTTAGAAAGAAAAGC
 A  A  L  L  A  G  R  N  N  Q  K  E  V  R  Q  Q  H  L  K  E  A  V  E  R  G  I  A  G  L  E  K  K  S
```

FIG. 4c

```
         310         320         330         340         350         360         370         380         390         400
          |           |           |           |           |           |           |           |           |           |
AGGGCCATCAGTCCTAAGGAAAAGAAAATCGTCGCCTACCATGAAGGGGGCATGCCGTGATTCTGAATGACTAAAGGGAGTGCTAGGGTGAATAAAG
 R  R  I  S  P  K  E  K  K  I  V  A  Y  H  E  S  G  H  A  V  I  S  E  M  T  K  G  S  A  R  V  N  K 410         420         430         440         450         460         470         480         490         500
          |           |           |           |           |           |           |           |           |           |
TTTCTATCATTCCAAGGGGCATGGGGCTTTAGGCTACACCCCTTAACACGCCTGAAGAAAAACAAATACTTGATGCAAAACACGAACTCATCGCTGAAAT
 V  S  I  I  P  R  G  M  A  A  L  G  Y  T  L  N  T  P  E  E  N  K  Y  L  M  Q  K  H  E  L  I  A  E  I 510         520         530         540         550         560         570         580         590         600
          |           |           |           |           |           |           |           |           |           |
TGATGTGCTTTAGGCGGAAGAGCGGCTGAAGATGTCTTTTGAAGAAATTTCTACCGGTGCGAGCAACGATTAGAAAGAGCGACTGATATTATTAAA
 D  V  L  L  G  G  R  A  A  E  D  V  F  L  E  E  I  S  T  G  A  S  N  D  L  E  R  A  T  D  I  I  K 610         620         630         640         650         660         670         680         690         700
          |           |           |           |           |           |           |           |           |           |
GGCATGGTGAGTTACTACGGCATGAGCAGTGTCAGTGGCTTAGTGTTAGAAAAGCAACGAACGCCTTTTAGGAGGCGGTTATGGAAGCAGTAGGG
 G  M  V  S  Y  Y  G  M  S  S  V  S  G  L  M  V  L  E  K  Q  R  N  A  F  L  G  G  G  Y  G  S  S  R 710         720         730         740         750         760         770         780         790         800
          |           |           |           |           |           |           |           |           |           |
AATTTAGCGAAAAACCGGAAGAAATGGATCTTTTCATTAAAAACTTGCTAGAAGAGCGCTATGAGCATGTCAAACAAACCTTGAGCGACTACAGAGA
 E  F  S  E  K  T  A  E  E  M  D  L  F  I  K  N  L  L  E  E  R  Y  E  H  V  K  Q  T  L  S  D  Y  R  E 810         820         830         840         850         860         870         880         890         900
          |           |           |           |           |           |           |           |           |           |
AGCGATTGAAATCATGGTCAAAGAATTGTTTGACAAAGAAGTCATTACAGGCGAAATACGAAGTTGCCAACAATTTA
 A  I  E  I  M  V  K  E  L  F  D  K  E  V  I  T  G  E  R  V  R  E  I  I  S  E  Y  E  V  A  N  N  L 
```

```
TTCAATATCAGCACCAACACAAGCGACCCCTATCTTTATCGGTATCCCCATTCCTGCGGGCGTATTGGTGGTGCTTTGTGTTATTGGATAACA
 F  N  I  S  T  N  T  S  D  P  Y  S  F  I  G  I  P  I  P  A  A  A  V  L  V  V  L  C  V  L  L  D  N

AATACCATTTTTAGAAGGAAATACCGAAAAGTTATTTTGTTATTGGGGTGCTTATGTGAGCAATATCCGCTACCCTAATTTTAA
 K  Y  H  F  L  E  G  N  T  E  K  L  F  L  S  F  I  V  L  L  G  V  L  M  V  S  N  I  R  Y  P  N  F  K

AAAAGTCAAATGAATCTCAAGCTTTTTATCTTAGTGTTGATTTTTATCGTTAGTGTTGTGCCCCTTAGAGGCTTAAGGCGTGTTATGGGGTTG
 K  V  K  W  N  L  K  L  F  L  V  L  I  F  L  S  L  V  F  V  R  P  L  E  A  L  S  V  F  M  G  L
 M  E  S  Q  A  F  Y  L  S  V  D  F  F  I  V  S  V  C  A  P  F  R  G  F  K  R  V  Y  G  V

TATTGATTTATGGCATCATTCGGTGGCTTTTTATTTTAATGGTAAAATTATTTTAATAAAATAAAAGTGCATGAAAGAATCTTTTACATAGAGGGAAT
 Y  L  I  Y  G  I  I  R  W  L  F  L  M  V  K  I  I  F  N  K  N  S  A  -
 V  F  D  L  W  H  H  S  V  A  F  F  N  G  K  N  Y  F  -  -     M  K  E  S  F  Y  I  E  G  M

GACTTGCACGGCGTGTTCTAGCGGATTGAACGCTCTTAGGGCGTAAGAGTTTTGTGAAAAATAGAAGTGAGCCTTTAAATAAGAGCCTAACATT
 T  C  T  A  C  S  S  G  I  E  R  S  L  G  R  K  S  F  V  K  I  E  V  S  L  L  N  K  S  A  N  I

GAATTTAACGAAATGAAACCAATTAGACGAGATTTAAACTCATTGAAAAACTGGGTATAGCCCTAAAAAAACTCTAGCAGAAGAAAAAAAGAAT
 E  F  N  E  N  E  T  N  L  D  E  I  F  K  L  I  E  K  L  G  Y  S  P  K  K  T  L  A  E  E  K  K  E
```

FIG. 4f

```
2110                2120                2130                2140                2150                2160                2170                2180                2190                2200
TTTTAGCCCTAATGTTAAATTAGCCGTTGGCGTTATTTTCACGCTTTTTGTGTATCTTTCTACGGGGCGATGCTTAGTCCTAGCCTTTACCTGA
 F  F  S  P  N  V  K  L  A  L  A  V  I  F  T  L  F  V  V  Y  L  S  M  G  A  M  L  S  P  S  L  L  P  E 2210                2220                2230                2240                2250                2260                2270                2280                2290                2300
AAGCTTGCTACGATTAACAACCATAGTAATTTTTTAAACGCATGCTACAGCTTCATTGTCATGCATTAGGAGGAGGATTTTACATT
 S  L  L  T  I  N  N  H  S  N  F  L  N  A  C  L  Q  L  I  G  T  L  I  V  M  H  L  G  R  D  F  Y  I 2310                2320                2330                2340                2350                2360                2370                2380                2390                2400
CAAGGGTTTAAAGCCTTATGGCACAGACAACCCAACATGAGTAGCCTTATCGCCATAGGCACAAGCCTGCCTTAATCTCAAGCTTGTGGCAATTGTATT
 Q  G  F  K  A  L  W  H  R  Q  P  N  M  S  S  L  I  A  I  G  T  S  A  A  L  I  S  S  L  W  Q  L  Y 2410                2420                2430                2440                2450                2460                2470                2480                2490                2500
TCGTTTATACAAGCCAGTGGTCTTATGGGCATTATTATTTGAAAGCGTGCGTGATTTAATGTTTGTAATGTGGGCAAACGCATTGAAAATGTTTC
 F  V  Y  T  S  Q  W  S  Y  G  H  Y  Y  F  E  S  V  C  V  I  L  M  F  V  M  V  G  K  R  I  E  N  V  S 2510                2520                2530                2540                2550                2560                2570                2580                2590                2600
TAAAGACAAAGCTTTAGACGCTATGCAAGCCTTGATGAAAAATGCACATAAAATGCAATAACCAACAGATTGAAGTTTTAGTGGAT
 K  D  K  A  L  D  A  M  Q  A  L  M  K  N  A  P  K  T  A  L  K  M  H  N  N  Q  Q  I  E  V  L  V  D 2610                2620                2630                2640                2650                2660                2670                2680                2690                2700
AGCATTGTGTGGGGATATTCTAAAGGTTCTCCCTGGAAGCGCGATTGCCGGTGGATGGCGAAATCATAGAGGGCGAAGGGAATTAGATGAAAGCATGT
 S  I  V  V  G  D  I  L  K  V  L  P  G  S  A  I  A  V  D  G  E  I  I  E  G  E  L  D  E  S  M
```

FIG. 4g

```
2710       2720       2730       2740       2750       2760       2770       2780       2790       2800
  |          |          |          |          |          |          |          |          |          |
TAAGCGGCGAAGCGTTGCCGGTTTATAAAAAGTCGGCGGATAAAGTCTTTTCAGGACATTCAATAGCCACGAGTTTTTAATGAAAGCCACGCAAGA
 L  S  G  E  A  L  P  V  Y  K  K  V  G  D  K  V  F  S  G  T  F  N  S  H  T  S  F  L  M  K  A  T  Q  D 2810       2820       2830       2840       2850       2860       2870       2880       2890       2900
  |          |          |          |          |          |          |          |          |          |
TAACAAAAACAGCACCTTGTCTCAAATTGTAGAAATGATCCATAACGCTCAAAGGCTCAGAGATTTCTGCCTAGCGGATAAGGTTCAAGCGTG
 N  K  N  S  T  L  S  Q  I  V  E  M  I  H  N  A  Q  S  S  K  A  E  I  S  R  L  A  D  K  V  S  S  V 2910       2920       2930       2940       2950       2960       2970       2980       2990       3000
  |          |          |          |          |          |          |          |          |          |
TTTGTGCCAAGCGGTGATCGCTATCGCTATTTTAGCGTTTGTGGTGGCTCATCATCGCGCCTAAACCCGATTTTTGGTGGAATTTGGAATCGCTTAG
 F  V  P  S  V  I  A  I  A  I  L  A  F  V  V  W  L  I  I  A  P  K  P  D  F  W  W  N  F  G  I  A  L 3010       3020       3030       3040       3050       3060       3070       3080       3090       3100
  |          |          |          |          |          |          |          |          |          |
AAGTGTTTGTATCGGTTTAGTGATTTCTGCCCTTGCGCCTTAAGGATTGGCTACACCTATGAGTATTTAGTAGCGAACCAAAAGCGAGTTCTTAGG
 E  V  F  V  S  V  L  V  I  S  C  P  C  A  L  G  L  A  T  P  M  S  I  L  V  A  N  Q  K  A  S  S  L  G 3110       3120       3130       3140       3150       3160       3170       3180       3190       3200
  |          |          |          |          |          |          |          |          |          |
TTTATTTTTAAAGACGCTAAAAGTTTAGAAAAAGCAAGGCTAGTCAATACGATCGTTTTGATAAAACCGGCACGCTCACTAACGGGACAAGCCTGTCGTT
 L  F  F  K  D  A  K  S  L  E  K  A  R  L  V  N  T  I  V  F  D  K  T  G  T  L  T  N  G  K  P  V  V 3210       3220       3230       3240       3250       3260       3270       3280       3290       3300
  |          |          |          |          |          |          |          |          |          |
AAAAGCGTTCATTCTAACATAGAATTATTAGAGTTAGTTGAGCGGGCAGTATTGAAAAGAGCAGCGAACATGTCATTGCTAAAGGATTGTAGAAT
 K  S  V  H  S  N  I  E  L  L  E  L  L  S  L  A  G  S  I  E  K  S  S  E  H  V  I  A  K  G  I  V  E
```

FIG. 4h

```
3310                3320                3330                3340                3350                3360                3370                3380                3390                3400
   |                   |                   |                   |                   |                   |                   |                   |                   |                   |
ACGCCAAAGAGAGCATAACGCTCCCTTAAAGAGTGAAGTAAAGTGAAAACAGATTATCAAGGCGCTAAAGA
 Y  A  K  E  H  N  A  P  L  K  E  M  S  E  V  K  V  K  T  G  F  G  I  S  A  K  T  D  Y  Q  G  A  K  E 3410                3420                3430                3440                3450                3460                3470                3480                3490                3500
   |                   |                   |                   |                   |                   |                   |                   |                   |                   |
GGTTATCAAAGTCGGTAATAGCGAATTTTTTAACCCTATTAACGACTAGAAATCAAGAAAACGGATTTAGTGTTTGTGGGTAGAGTGATCAGTGAA
 V  I  K  V  G  N  S  E  F  F  N  P  I  N  A  L  E  I  Q  E  N  G  I  L  V  F  V  G  R  V  I  S  E 3510                3520                3530                3540                3550                3560                3570                3580                3590                3600
   |                   |                   |                   |                   |                   |                   |                   |                   |                   |
AAAGAAGACGAGCTTTTAGGGGCGTTTGTTTTAGAAGATTGCCCAAAAAAGGCGTGAAAGAGCATATCGCTCAAATCAAAAAATTAGGCATTAACACTT
 K  E  D  E  L  L  G  A  F  V  L  E  D  L  P  K  K  G  V  K  E  H  I  A  Q  I  K  K  L  G  I  N  T 3610                3620                3630                3640                3650                3660                3670                3680                3690                3700
   |                   |                   |                   |                   |                   |                   |                   |                   |                   |
TTCTTTTTAAGCGGGGACAATAGAGAGAATGTCAAAAAATGCGCGCTTGAATTAGGAGGATTGATGGTTATATCAGCAACGCTAAACCACAAGACAAGCTCAA
 F  L  L  S  G  D  N  R  E  N  V  K  K  C  A  L  E  L  G  I  D  G  Y  I  S  N  A  K  P  Q  D  K  L  N 3710                3720                3730                3740                3750                3760                3770                3780                3790                3800
   |                   |                   |                   |                   |                   |                   |                   |                   |                   |
CAAGATCAAAGAGCTTAAGGAGAAAAGGGGCAGATCGTTATGATGGTTGGTGATGGCTTGAATGACGCTCCTAGCCTTGCTATGAGCGATGTGCCAGTGGTG
 K  I  K  E  L  K  E  K  G  Q  I  V  M  M  V  G  D  G  L  N  D  A  P  S  L  A  M  S  D  V  A  V  V 3810                3820                3830                3840                3850                3860                3870                3880                3890                3900
   |                   |                   |                   |                   |                   |                   |                   |                   |                   |
ATGGCTAAAGGGAGCGATGTGAGCGTGCAAGCAGCGGATATTGTGAGCTTTAATAACGACATTAAATCGGTTATAGCGCGATTAAATTGAGCCAAGCCGA
 M  A  K  G  S  D  V  S  V  Q  A  A  D  I  V  S  F  N  N  D  I  K  S  V  Y  S  A  I  K  L  S  Q  A
```

FIG. 4i

```
      3910        3920        3930        3940        3950        3960        3970        3980        3990        4000
CCATCAAAAATATCAAAGAAATTTGTTTGGGCTTTTTGTTATAATAGCGTGTTATCCCTTAGCTGTGGGGTTCTTATAAAGCTAATCATGTT
 T   I   K   N   I   K   E   N   L   F   W   A   F   C   Y   N   S   V   F   I   P   L   A   C   G   V   L   Y   K   A   N   I   M   L 4010        4020        4030        4040        4050        4060        4070        4080        4090        4100
AAGCCCGGCGATTGCGGGGTTAGCGATGAGTTAAGCTCTGTGAGTGTGGTCTAAACTCCCAAGGCTAAGGAATTTAAAATTAAGGATCATTGAATG
 S   P   A   I   A   G   L   A   M   S   L   S   S   V   V   S   V   V   L   N   S   Q   R   L   R   N   F   K   I   K   D   H   -   M 4110        4120        4130        4140        4150        4160        4170        4180        4190        4200
AAAGTTACTTTCAAGTGCCAAGCGTGGTTGTAGAATTTGACGCTCCAGCGACACAGGATTTGATTAAGGAAGCCTTATTGATGCGA
 K   V   T   F   Q   V   P   S   I   T   C   N   H   C   V   D   K   I   E   K   F   V   G   E   I   E   G   V   S   F   I   D   A 4210        4220        4230        4240        4250        4260        4270        4280        4290        4300
GCGTGGAAAAAGAGCGTGGTTGTAGAATTTGACGCTCCAGCGACACAGGATTTGATTAAGGAAGCCTTATTGGATGCGGGCCAAGAAGTAATATAATA
 S   V   E   K   K   S   V   V   V   E   F   D   A   P   A   T   Q   D   L   I   K   E   A   L   L   D   A   G   Q   E   V   I   -   -

4310        4320        4330        4340        4350        4360        4370        4380        4390        4400
AAGGTGTGTGATATAGAAGTATCGGATTAAAACCCAACATTCAAAAGGGTTGTATCTTTAATTCTTGGGTTTGTTGGTATTTCACGCCCTTCA 4410        4420        4430        4440        4450        4460        4470        4480        4490
ATGGTGATTTATCATAACCATAAGAGAAAAATTATCGTATTTCCCCCTTTTCTTACTCCAATTTTTTATACATACGGATCTCGAGGTACCCGGG
 M   V   I   Y   H   N   H   K   R   K   N   Y   R   I   S   P   F   S   Y   S   N   F   L   Y   I   R   I
```

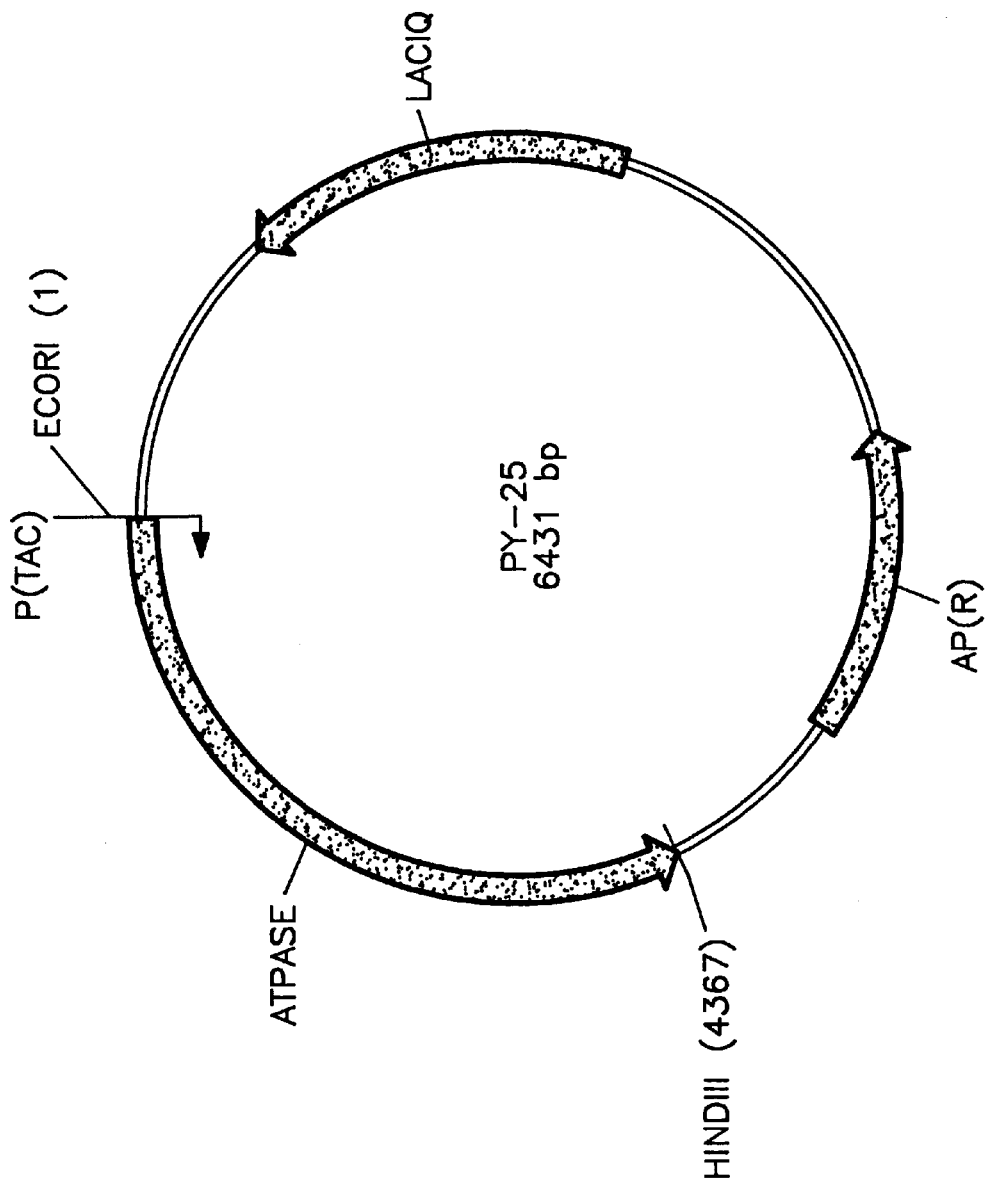

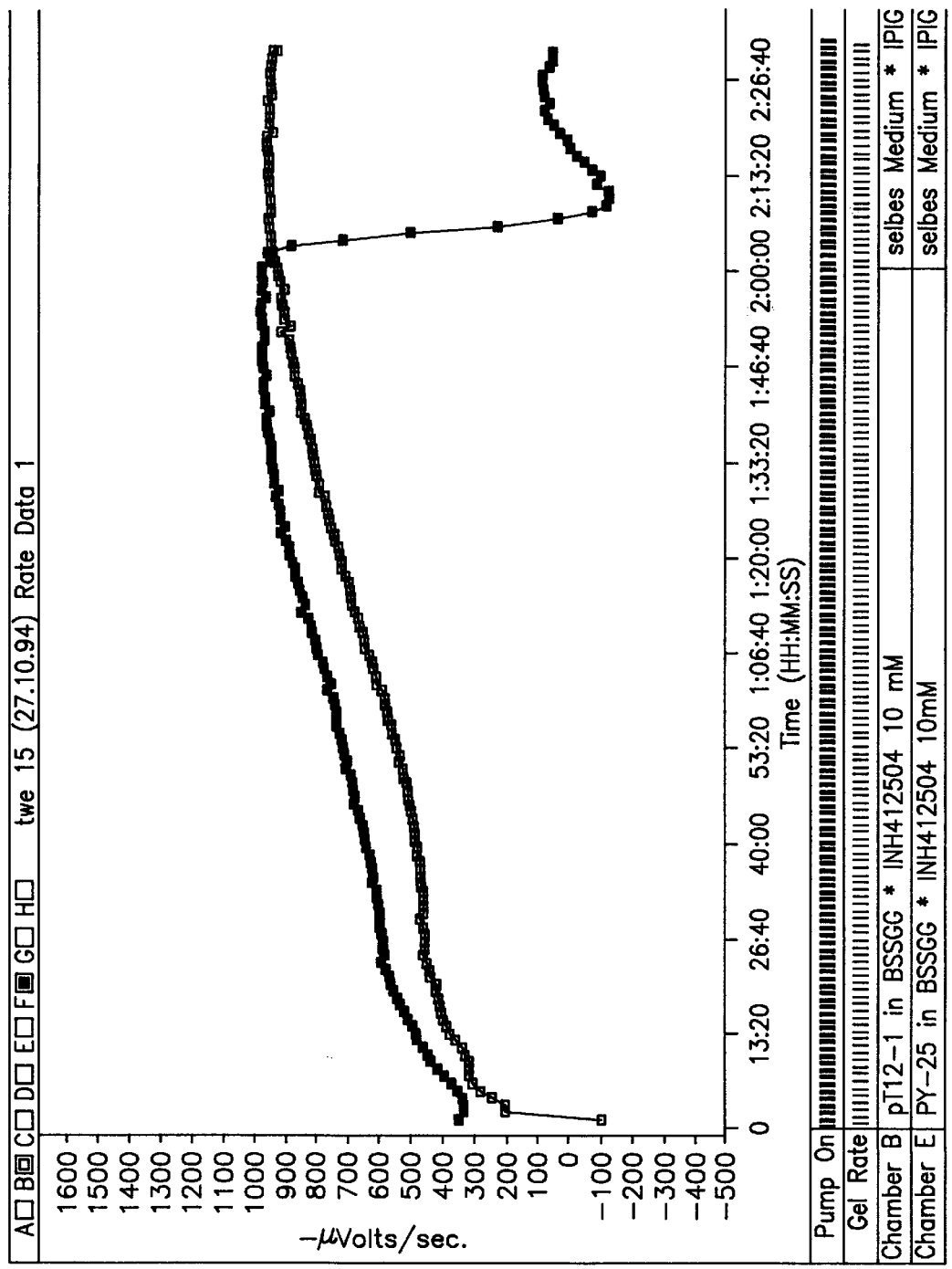

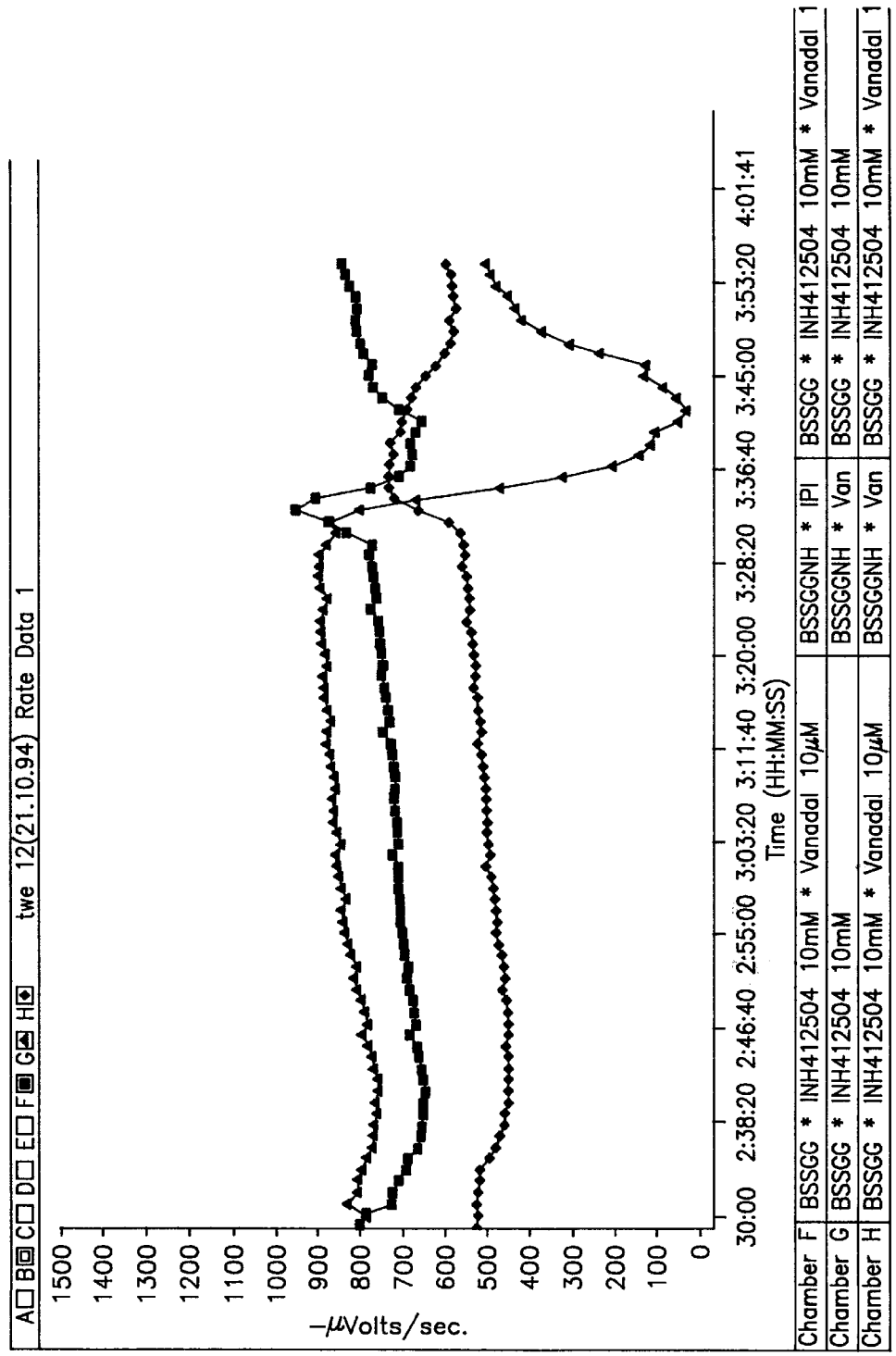

SCREENING KIT AND PROCESS FOR DETERMINING ACTION OF SUBSTANCES INHIBITING THE P-TYPE ATPASE ACTIVITY OF *HELICOBACTER PYLORI*

TECHNICAL FIELD

The invention relates to a screening model for the determination of the action of substances inhibiting the P-ATPase activity of Helicobacter.

PRIOR ART

*Helicobacter pylori* (*H. pylori*) is a human-pathogenic, gastric bacterium whose eradication from the stomach is today considered an obligatory requirement for the lasting cure of *H. pylori*-associated diseases. The microorganism is found in the stomach, preferably in and under the mucous membrane, occasionally also between the epithelial cells. Owing to the uniqueness of the medium in which the microorganism is found, *H. pylori* must have developed metabolic/physiological strategies which make possible its survival in the gastrointestinal region of man.

It is known today that the occurrence of the microorganism often is causally associated with the development of gastritis, ulcer and certain forms of stomach cancer. The forms of therapy customary today are based on the administration of substances which inhibit the activity of the gastric proton pump, $H^+/K^+$-ATPase, together with substances having antibiotic activity, which on the one hand are not always understood as regards mechanism of action and on the other hand comprise the risk of the formation of resistance. On account of the wide distribution of the microorganism and of the unsatisfactory therapeutic strategies to date, the need for new therapeutic strategies is therefore great.

Primary screening for helicobactericidal substances is based today, on the one hand, largely on in vitro methods such as the agar dilution test, using which the minimum inhibitory concentration with respect to *H. pylori* growth can be determined. In addition, Helicobacter-infected animals are often employed as an in vivo model for the screening of helicobactericidal substances. In both cases this necessitates the relatively complicated handling of the microorganism, which on the one hand is distinguished by relatively slow growth, which is why relatively long breeding or culturing times are needed, and on the other hand by demanding media conditions (microaerophilia, serum addition is necessary). Moreover, *H. pylori* is a human pathogen (classified as S2 according to the German State Contagious Diseases Act) and handling is therefore associated with appropriate safety measures and restrictions. In the development of helicobactericidal medicaments, the need for simple in vitro primary screening models, with the aid of which the use of experimental animals in the primary screening phase can also be reduced, is great. Such screening models can be the basis for the development of suitable, safe and efficient forms of therapy for the eradication of this human-pathogenic bacterium. In order to guarantee a safe and, if possible, Helicobacter-specific action, it should be possible to describe the targets of future eradication strategies, if possible, in their molecular structure and biochemical-physiological significance for the microorganism. On the basis of recombinant screening models, in which the action of drugs on cloned Helicobacter functions can be investigated, the development and improvement of drugs taking into account drug-target interactions into the molecular region is possible.

DESCRIPTION OF THE INVENTION

One object of the invention is to be seen in making available a screening model which, without specific safety restrictions and without the use of experimental animals, allows the primary screening of substances having Helicobacter-inhibiting action.

It has now been found that the measurement of the metabolic activity of a recombinant organism which is transformed using at least one Helicobacter-specific P-ATPase gene controllable via a promoter in the presence of cations which inhibit the metabolic activity of the recombinant organism only together with Helicobacter P-ATPase can be used for the effective and highly selective determination of the Helicobacter-inhibiting action of substances to be investigated.

One subject of the invention is therefore a screening model for the determination of the action of substances inhibiting the P-ATPase activity of Helicobacter, comprising a) a recombinant organism consisting of host cells transformed using at least one P-ATPase gene controllable via a promoter,
b) an inducer for the genetic activation of the P-ATPase,
c) cations which impair the metabolic activity of the recombinant organism only in the presence of Helicobacter P-ATPase, and
d) a measuring device for the determination of the metabolic activity of the recombinant organism.

Further subjects follow from the subclaims.

From the *H. pylori* genome, DNA fragments were isolated which code for plasma membrane-associated ATPases of the P type, in the following called P-ATPases or Helicobacter P-ATPases. The ATPases 439 and 948 in particular were more closely investigated. The Helicobacter P-ATPase genes were purified, cloned, sequenced and functionally expressed in transformed *E. coli*. The function or activity of the heterologous gene products interferes with the metabolic activity of the recombinant microorganism, such as, for example, with the proton concentration in the immediate environment of the cells, and can therefore be detected by measurement. The recombinant organisms which express the specific P-ATPase gene can be used to detect (screening) biological and/or chemical compounds which affect, preferably inhibit, the activity of the HP-P-ATPase and to optimize the action on Helicobacter.

The host vector system allows screening for substances which interact with the cloned ATPase, without primarily having to work with *H. pylori,* which is relatively complicated to culture, and is an organism classified according to safety stage S2.

In addition, on this basis, by means of the expression of specifically mutated ATPase sequences the molecular interaction between protein (target) and inhibitor can be specifically analyzed (elucidation of the mechanism of action of binding). The system thus also offers the basis for a specific design of inhibitors (drug development).

The isolation of the ATPase genes from the *H. pylori* genome and their insertion into bacterial expression vectors and cloning are carried out by methods known per se.

The host cells used were preferably derivatives of *E. coli* K12, *E. coli* MM294 being preferred.

Possible bacterial expression vectors are the customary, commercially available plasmids for bacterial expression. In this connection, the hybrid tac promoter from the lac/trp system is preferred, but further promoters such as, for example, trc, lac or trp can also be employed. pT12-1, in particular, which is described in detail in chapter 3.1.2, is also suitable as an expression plasmid.

The model according to the invention for screening for substances which inhibit the P-ATPase activity of Helicobacter consists of a recombinant organism, transformed using at least one Helicobacter P-ATPase gene which is expressed by a promoter. The synthesis of the P-ATPase leads in the host cell to a sensitivity to media which besides C or N sources contain a number of ions, among them $NH_4^+$ ions. This P-ATPase mediated sensitivity of the host cell manifests itself phenotypically by an immediate and significant decrease or change in the cellular metabolic activity, which can be detected by measurement. This effect on the cellular activity of the recombinant organism, which is only found with expression of the Helicobacter P-ATPase(s) can be prevented, for example, by ortho-vanadate, an inhibitor of P-ATPases. The model is therefore suitable for the screening and for the improvement of specific inhibitors of Helicobacter P-ATPase(s), which specifically interact with the Helicobacter P-ATPase activity.

The function of the model is shown below by example of a recombinant organism which consists of an E. coli K12 host cell and a recombinant expression plasmid. A P-ATPase which was isolated from H. pylori (HP) was inserted into the plasmid. In computer-assisted homology analysis, the derived amino acid sequence of the P-ATPase gene shows significant similarity to bacterial and eukaryotic P-ATPases which are already known, in particular to those whose function is the transport of divalent cations. The gene or gene product is a possible target for a differential drug therapy of H. pylori-associated diseases. The gene or its recombinant expression in other organisms makes possible the screening and the detection of substances which affect, preferably inhibit, the specific gene and/or the correlating gene function in their activity.

The present invention makes possible specific and selective primary screening on the basis of a specific Helicobacter function (P-ATPase activity) with the aid of recombinant organisms which are classified as non-human-pathogenic and from their handling are clearly more undemanding. Since P-ATPases are of essential importance for the medium- or microorganism-specific ion balance of bacterial organisms such as H. pylori, these are highly selective targets for differential Helicobacter therapy, by means of which the microorganism in its natural habitat can be decisively inhibited in its vital integrity by means of appropriate compounds and destroyed.

All parameters known as a measure of the metabolic activity of bacterial cells are suitable for the measurement of the metabolic activity of the recombinant organism. In connection with the present invention, the determination of the pH in the immediate environment of active cells is in particular suitable. Commercially available cytosensor microphysiometers (Molecular Devices, Grafelfing) are particularly suitable for the measurement. As a measure of the metabolic activity, the acidification rate, i.e. the rate at which the medium is acidified by the cellular metabolic activity, is used.

EXPERIMENTAL

The working steps and methods described relate in particular to the isolation, analysis, cloning and expression of DNA. These methods are well understood and have been described in their nature and technique. The experimental work was carried out according to these known methods of genetic or molecular biology (Molecular Cloning, Maniatis et al., Cold Spring Harbor Laboratory Press, 1989). The computer-assisted analysis of DNA sequences obtained for the detection of ORFs (Open Reading Frames), homology investigations etc. can be carried out using genetic computer programs and databases (e.g. DNASIS/PROSIS, PC-Gene, UW-GCG) available in a wide variety.

1. Isolation of DNA fragments from the H. pylori genome, which contain the P-type ATPase genes and adjacent DNA regions having further Helicobacter genes 1.1 Description of the gene probe At the beginning of the studies, no P-ATPases had been isolated from the HP genome and corresponding DNA sequence information was therefore not available. A homology comparison of P-ATPase sequences from other pro- and other eukaryotic organisms show that this class of enzyme, in addition to a considerable structural homology, also has regions in which the amino acid (AA) primary sequences are present in highly conserved form. A particularly conserved region whose existence gives its name to this class of membrane ATPases is the phosphorylation site (P site) of the P-ATPases. A DNA oligonucleotide (I282) which represents a selected subpopulation of 16 DNA sequence variations from more than 2000 possible variations was derived from the AA primary sequence of the P site. The 20 bp oligonucleotide I282 is a mixture of 16 different DNA sequences which code for the DKTGT(I/L)T (SEQ ID NO: 12) consensus sequence of P-ATPases. The amino acid sequence is indicated below by means of the DNA sequence of the DNA oligonucleotide in the single letter and three-letter code:

```
    D    K    T    G    T    I/L    (T)     (SEQ ID NO:13)

Asp  Lys  Thr  Gly  Thr  Ile    (Thr)

Leu

5' - GAT  AAA  ACC  GGC  ACC  ATC   AC - 3'

A                   G T  G
```

The DNA oligonucleotide I-282 labeled with digoxigenin was first employed in Southern blot analyses using genomic DNA from HP and E. coli which had previously been digested by the restriction endonucleases EcoR1, Hind3 or Ava2. The DNA oligonucleotide hybridized efficiently with the HP-DNA and therefore showed itself to be suitable for subsequent gene screening. I-282 also hybridized with the E. coli DNA, which was of particular importance for the screening strategy.

Further DNA oligonucleotides which code for the DKTGT(I/L)T consensus sequence of P-ATPases (P region/P site) were derived from the AA primary sequence of the P consensus region. These derived 20 bp-long DNA probes represent various subpopulations and thus DNA sequence variations of the P region. They correspond in their length to the DNA oligonucleotide I-282. I-405 to I-409 correspond to the total DNA sequence pool which comprises all possible sequences of this region. These oligonucleotides can be employed correspondingly to the procedure in the case of I-282 for the detection and isolation of potential P-type genes by use of the customary labeling and hybridization methods.

The DNA sequences of the DNA oligonucleotide mixtures (DNA probes I-405, I-406, I-407, I-408 and I-409) in the 5'→3' position are indicated below:

GA(TC) AA(AG) AC(AGCT) GG(AGCT) AC(AGTC) AT(TC) AC is I-405 (SEQ ID NO: 14),

GA(TC) AA(AG) AC(AGCT) GG(AGTC) AC(AGTC) AT(CA) AC is I-406 (SEQ ID NO: 15),

GA(TC) AA(AG) AC(AGCT) GG(AGTC) AC(AGTC) TT(AG) AC is I-407 (SEQ ID NO: 16),

GA(TC) AA(AG) AC(AGCT) GG(AGTC) AC(AGTC) CT(TC) AC is I-408 (SEQ ID NO: 17), and GA(TC)AA(AG)AC(AGCT)GG(AGTC)AC(AGTC)CT (AG)AC is (SEQ ID NO: 18) DNA oligonucleotide I-409.

Positions in brackets with several bases represent variable positions. The molecules were labeled for the hybridization experiments using the digoxigenin 3'-end labeling kit (Boehringer Mannheim) according to the procedure of the manufacturer. It is seen from the direct sequence comparison of these DNA oligonucleotides (I-405 to I-409) with the base sequence and complexity of the DNA Probe I-282 that the probes I-405 to I-409 are each distinctly more degenerate (i.e. more variable in their sequence). The higher complexity of these probes should make it possible, if these are all used, to isolate the total P-type ATPase family. Owing to the increased degeneration of the probes in comparison with I-282, the risk of the isolation of "false-positive" plasmids from the H. pylori gene bank, which, however, can be separated clearly from the P-type ATPase genes at the level of DNA sequencing, is admittedly increased.

If a certain P-type ATPase is isolated from the H. pylori genome only for the first time using a DNA oligonucleotide, on the basis of the clear sequence information obtained a reisolation of further copies can be specifically carried out, the known standard methods of molecular biology in turn being used. This course of action is particularly advantageous if only a partial DNA sequence of a P-type ATPase is present on an isolated plasmid.

1.2 Description of the HP Gene bank

The HP gene bank was constructed and made available by Dr Rainer Haas (Tübingen).

The HP gene bank was set up starting from HP Isolate 69A. To do this, chromosomal DNA was isolated from HP69A and partially digested by Sau3A. DNA fragments of >3 kb were enriched by gel electrophoresis.

The cloning vector employed was pRH160 (FIG. 1), which has a tetracycline resistance marker (Tet®). The 2.44 kb plasmid additionally has a unique Bgl2 cleavage site in the polylinker region. This Bgl2 site was used for the cloning of the HP-DNA fragments. The recombinant plasmids were transformed and cloned in E. coli HB101. $2 \times 10^4$ independent transformants were obtained. After amplification, 200 µl aliquots each containing $3.7 \times 10^6$ cfu (colony-forming units) were dispensed and stored. The HP-DNA insertions inserted into the plasmid can be excised again from the vector by means of a double digestion with EcoR1 and Xho1.

1.3 Plasmid pRH439

1.3.1. Isolation of pRH439

Since the DNA probe I-282 also reacts with E. coli DNA (1.1), screening was carried out directly on the plasmid DNA. To do this, an aliquot from the gene bank was diluted and distributed as an inoculum in 20 culture tubes such that approximately 70 independent clones from the gene bank were represented in each tube.

Altogether, 1400 clones (of the 20,000 present) of digoxigenin-labeled oligonucleotide I-282 were searched for P-ATPases by this procedure. With an average size of the HP-DNA insertions of about 3000 bp, the 1400 plasmids represented approximately 2–3 H. pylori genome equivalents.

A plasmid preparation was in each case prepared from the 20 "mixed plasmid cultures". An aliquot of the bacterial cultures was frozen out as a glycerol preserve. After restriction with EcoR1/Xho1, the plasmid preparations were subjected to a Southern blot analysis using I-282 as a probe. The plasmid mixture No. 4 yielded a clear signal here. An aliquot of the corresponding glycerol preserve was therefore plated on LB agar plates. Plasmid preparations of randomly selected colonies were again prepared, which as in the primary screen were investigated by Southern blot analysis. In this connection, the plasmid preparation No. 39 proved to be positive. This course of action led to the isolation of plasmid pRH439.

1.3.2. Sequence analysis of the isolated plasmid pRH439

The plasmid carries an HP-DNA insertion of length about 3.4 kb, which can be excised with EcoR1-Xho1. DNA sequencing led to the result that the HP-specific DNA fragment contains an ORF (open reading frame) of 2058 bp. This codes for a protein of 686 amino acids. The DNA sequence (SEQ ID NO: 1) contained and the amino acid sequence (SEQ ID NO: 4=AtPase 439) resulting therefrom are shown in FIGS. 2a–e.

The polypeptide chain contains in position D-388 (Asp-388) to T-394 (Thr-394) the conservative box used for the isolation of the gene, which contains the P-site characteristic of P-ATPases. The hydrophobicity analysis shows whole series of possible transmembrane helices, which are necessary for the specific membrane topology of the enzyme and are characteristic of P-ATPases and other membrane enzymes.

A particular feature of the isolated HP-ATPase, differing from the previously isolated P-ATPases, is the high concentration of cysteine and histidine residues. Cys and His residues occur on a huge scale in the range of AA positions 420 to 550. In addition, the enzyme is distinguished by an N-terminal HIHNLDCPDC (SEQ ID NO: 19) ion-binding site and has an internal CPC motif.

In the Helicobacter-specific DNA insertion of the plasmid pRH439, before the ATPase gene (ATPase 439) was found an additional ORF which is terminated by the cloning site and is therefore incomplete. The Helicobacter-specific DNA insertion of pRH439, however, overlaps at the 5' end with the insertion of plasmid pRH514, so that with the aid of the plasmid pRH514 the ATPase associated ORF can be completed.

1.4. Plasmid pRH514

1.4.1. Isolation of pRH514

This plasmid was isolated from the H. pylori 69A gene bank as described for pRH439. However, the probe employed was the DNA oligonucleotide I-407.

Sequencing of the H. pylori-specific DNA insertion of pRH514 showed that this comprises 3097 bp. The DNA (SEQ ID NO: 2) sequence and the amino acid sequence (SEQ ID NO: 5=ATPase Associated Protein 514) of the complete ORF are shown in FIG. 3.

1.4.2 Sequence analysis of the isolated plasmid pRH514

The DNA sequence was determined by means of DNA sequencing. It emerged that the pRH514 insertion DNA extends the DNA sequence of the plasmid pRH439 to 5'. In this case, the reading frame in pRH439, interrupted by the cloning site, which precedes the P-type ATPase, is completed. Since this gene inserted before the ATPase codes for a protein product and is localized obviously adjacent to the described P-type ATPase on the chromosome of H. pylori 69A, the derived gene product was called an ATPase associated protein (AA protein, abbreviated: AAP).

The AAP-coding ORF of pRH514 predicts an amino acid chain consisting of 506 residues. 24 bp downstream follows the ORF for the ATPase 439, which is incomplete, however, in the 3' region on pRH514.

The AA protein is characterized by a significant homology to response regulators of bacterial two-component systems. These systems of signal transduction are generally made up of a membrane-continuous sensor kinase and a cytosolic response regulator protein. The AAP of H. pylori shows an identity of about 15–20% with E. coli NtrC and K.pneumoniae NifA, two known response regulator proteins, over the entire amino acid sequence.

H. pylori-AAP can be subdivided into three domains corresponding to the known response regulators: a regulative N-terminal domain having an aspartate residue in position 56, a central domain having a so-called Walker A ATP-binding motif (Gly-Ser-Pro-Gly-Cys-Gly-Lys-Ser (SEQ ID NO: 20)) and the C-terminal domain with helix-turn-helix motifs, which point to the possibility of interaction with DNA. It is conspicuous that the central domain of AAP contains four symmetrically arranged Cys residues (positions 358, 360, 370, 372).

1.5. pRH948

1.5.1. Isolation of pRH948

This DNA clone was isolated from the H. pylori gene bank by means of DNA probe I-408. The isolation strategy is described under 1.3.1.

1.5.2. Sequence analysis of the isolated plasmid pRH948

The plasmid contains an H. pylori-specific DNA insertion of about 4.5 kbp. The DNA sequence was determined by means of DNA sequencing. The DNA sequence contains 4 complete ORFs (ORFs 2–5) and 2 incomplete, terminal ORFs (ORF1 and 6). In FIG. 4, the complete DNA sequence (SEQ ID NO: 3) and the derived amino acid sequences of the corresponding ORFs are shown. ORF 4 codes for a further P-type ATPase of H. pylori, called ATPase 948 here.

1.5.3. Detailed description of ATPase 948 (ORF4)

Beginning from DNA base position 1872, the DNA contains an ORF (open reading frame) which codes for a protein consisting of 741 amino acids. The protein has the conserved phosphorylation site required for P-type ATPases. Sequence motifs which are characteristic of P-type ATPases, in particular from the family of the metal ion-transporting P-type ATPases, are contained in the pRH948 DNA aforementioned amino acid sequence (SEQ ID NO: 9=ORF 4, ATPase 948).

The protein comprises:

a conserved phosphorylation site
an ATP binding region
an N-terminal Cys-x-x-Cys sequence (SEQ ID NO: 21)
a Cys-Pro-Cys sequence, associated with a region of hydrophobic amino acids.

The DNA sequence and the amino acid sequence of the P-type ATPase coded by pH948 derived therefrom are shown in FIGS. 4a–i.

These sequence motifs were also found in the pRH439-encoded, Helicobacter-specific P-type ATPase described above.

ATPase 948 shows sequence similarities, in particular with ATPase 439 from H. pylori, the CopA/B-AtPases from Enterococcus hirae and the Cd pump from Staphylococcus aureus (about 30% sequence identity).

The 607 C-terminal amino acids are distinguished by a 93.7% sequence identity with the hpCopA-ATPase of H. pylori published by Tylor et al. However, the hpCopA gene product contains no N-terminal Cys-x-x-Cys motif and the putatively membrane-associated amino acid triplet Cys-Pro-Cys is likewise not present in hpCopA. Instead of this, the sequence Cys-Pro-Ser is found in hpCopA. The pRH948-encoded ATPase, however, has an N-terminal region with the characteristic amino acid sequence Cys-x-x-Cys.

The gene for ATPase 948 can be expressed in heterologous form like that of ATPase 439. To do this, methods and strategies described in detail in Chapters 2 and 3 are suitable. ATPase 948 is also suitable in particular as a base for the active compound screening model described in further detail by example of ATPase 439.

1.5.4. Description of the further ORFs localized on pRH948

The amino acid sequences of the various ORFs can be seen from FIG. 4.

ORF 1 codes for the C-terminal part of a protein and is therefore a C-terminal partial sequence (SEQ ID NO: 6=ORF 1). This comprises 309 amino acids beginning with an aspartate residue and ending with a serine. The sequence starts immediately at the start of the insertion DNA. In homology investigations, the derived protein product shows significant homology with so-called AAA-type ATpases, which also include the well-differentiated FtsH protein of E. coli.

ORF 2 (SEQ ID NO: 7) starts in base position 1162 of the DNA sequence of pRH948. The ATG start codon for methionine lies here. This ORF consisting of a total of 237 triplets ends in position 1872 with the last base of the terminal alanine triplet. The derived protein product is distinguished by significant homology to bacterial phosphatidylserine synthetases (PSS).

ORF 3 (SEQ ID NO: 8) is localized within ORF 2 in a frame-shifted manner. It begins with the base A in position 1710 as part of the ATG start codon and codes for a peptide of 48 amino acids.

ORF 4 codes for the P-type ATPase 948 already described above. This ORF begins in position 1872 of the DNA sequence. The last base of the ORFs coding for the PSS-homologous protein thus simultaneously represents the starting point of the coding sequence for the P-type ATPase. ORF 4 ends in position 4094. The terminating TGA stop codon follows immediately.

ORF 5 (SEQ ID NO: 10) follows immediately on the TGA stop codon of the P-type ATPase beginning with an ATG start codon (base positions 4098–4100). The ORF predicts a protein of 66 amino acids. The protein is characterized by a CxxC motif found in the N-terminal region, CNHC. It is homologous in comparison with the CopZ protein which in Enterococcus hirae is a constituent of the Cop operon.

ORF 6 (SEQ ID NO: 11) is incompletely present like ORF 1. It begins in position 4401 and terminates after 27 triplets terminated by the end of the Helicobacter-specific DNA sequence in pRH948.

2. Heterologous expression of Helicobacter genes

The isolated and characterized H. pylori genes can be expressed completely or in part in heterologous systems (bacteria, yeasts, eukaryotes). For bacterial systems, inter alia, the conventional expression plasmids with bacterial promoters such as, for example, lac, tac and trp are suitable. Suitable host cells are in particular E. coli k12 host cells and their derivatives. The heterologous expression of H. pylori genes is suitable for the identification and development of helicobactericidal active compounds and for the induction of antibodies and antisera.

The functional expression of essential H. pylori genes in E. coli is suitable for the construction of screening models with whose aid specific H. pylori enzyme activities can be selectively measured. Such models can be employed for the identification and development of substances which inhibit the cloned and heterologously expressed H. pylori proteins in their function and thus potentially have significance as helicobactericidal drugs in the therapy of Helicobacter-associated diseases.

The experimental procedure for the heterologous expression of H. pylori genes in E. coli for the construction of a screening model is shown in the following by example of the P-type ATPase 439, coded by pRH439.

This procedure leads to the functional and measurable expression of Helicobacter genes in a suitable host cell. The measurability of the Helicobacter-specific activity is based on a change in the total metabolic efficiency of the host cell.

It has now been found that the expression of an H. pylori P-type ATPase in E. coli significantly changes the metabolic activity. The system described in the following shows that the metabolic efficiency of the host cell, which can be detected by measurement, modified by the expression of the H. pylori gene product can be used for the identification of inhibitors of the specific Helicobacter activity. Active compounds which affect the isolated Helicobacter activity are detected in that these prevent or abolish the change produced in the metabolic efficiency of the host cell.

The region coding for the Helicobacter ATPase was amplified from plasmid pRH439 by means of polymerase chain reaction (PCR) and inserted and cloned in various bacterial expression vectors with E. coli tac, Trc or Trp promoters. These include, inter alia, the plasmids pTI2-1, pTrcHisA and PTrp233. In these vectors, the H. pylori P-type ATPase gene is under the control of the promoters indicated. The constructed plasmids were transformed in E. coli K12 strains. For expression, the recombinant E. coli strains were cultured and, before achieving maximum cell density, treated with the inducer (IPTG, isopropylthiogalactoside, for tac and Trc promoters or β-IAA, indoleacetic acid, for Trp promoters). The protein profile of the E. coli strains was analyzed by gel electrophoresis before and after induction. After gene induction, a new protein band occurs in the recombinant E. coli strains which runs in the gel at about 70 kDa. The procedure described below for the construction of functional expression vectors which allow the synthesis of recombinant Helicobacter proteins in E. coli is a basis or foundation for the construction of a screening model. The structure and function of the screening model are described in detail in the next chapter.

3. Description of the screening model

The model consists of a recombinant E. coli strain which on an expression plasmid carries the gene sequence of an H. pylori P-type ATPase which is controllable in its activity. The medium in which the measurement is carried out must be composed in such a way that the activity of HP-ATPases can be induced and measured therein. The activity of ATPases incorporated in the host cell has an effect on the general metabolic activity of the host cell and is therefore accessible to measurement. The change in the metabolic activity of the recombinant host cell induced by the P-type ATPase activity can be prevented by inhibition of the P-type ATPase activity. The latter is the basis for the use of the model for the screening and optimization of substances.

The function of the model is described in the following by example of the E. coli strain PY25.

3.1. Detailed description of the model components 3.1.1. Host cell

The host cell is E. coli MM294. This strain is an E. coli K12 derivative and is therefore classified as non-human-pathogenic.

3.1.2. ATPase expression plasmid

The expression vector is plasmid PY25. This is composed of the plasmid pTI2-1 and the HP-P-type ATPase gene 439.

pTI2-1 was constructed starting from the plasmids pKK223-3 and pGex2T, which were both obtained from Pharmacia. First the PstI cleavage site in the polylinker of pKK was deleted. To do this, pKK was cleaved using PstI and the ends were treated with T4-DNA polymerase. The vector was then digested with SmaI, religated and, after transformation, cloned in E. coli HB101. The cloning product is pKKδBamH1. The Amp® in pKKδBamH1 was replaced by the Amp® gene from pBR322, since the latter has an internal PstI cleavage site. To do this, pKKδBamH1 and also pBR322 were double-digested using PvuI and NdeI. The smaller band (about 1.45 kb) was isolated from the pBR322 digestion and the large band (about 3 kb) from pKKδBam. The two DNA fragments were ligated and cloned in E. coli HB101. The cloning product is pKK(Pst)δBam.

pKK(Pst)δBam1 was digested with PstI and SspI. The two small DNA bands of about 620 and 560 bp were isolated from an agarose gel. pGex2T was also digested with the enzyme combination Ssp1×Pst1. After electrophoretic separation in the agarose gel, the large 3.2 kb DNA fragment was isolated. The three isolated DNA fragments from pKK(Pst)δBam and pGex2T were ligated and cloned in E. coli HB101. The cloning product is pTI2. This vector contains a tac promoter, an Amp® gene and the lac repressor GenlacI$^q$. Plasmids of comparable structure can be obtained, for example, from Pharmacia (pTrc99A).

pTI2 was linearized using the enzyme combination EcoR1/Hind3 and ligated with the double-stranded DNA oligonucleotide MCS1 (Multi Cloning Site 1), which has the corresponding compatible EcoR1 or Hind3. After ligation and transformation, plasmid pTI2-1 was obtained. MCS1 is cloned here behind $P_{Tac}$ (tac promoter) in the EcoR1 site of pKK. After cloning in pTI2-1, MCS1 has the sequence 5'-GAATTCGTAG GAAGCTCATAT GGTCGACTC TAGACCCGGG CTGCAGAAGCTT-3' (SEQ ID NO: 22), which offers for cloning the restriction sites EcoR1, Nde1, Sal1, Xba1, Sma1, Pst1 and Hind3. In FIG. 5, a plasmid map of the constructed expression vector pTI2-1 is shown.

For the insertion of the HP-ATPase gene 439 in pTI2-1, DNA primers I-404 and I-402 with the sequences 5'-ACCGA CTTGA ATTCA TGCAA GAATA CCACA TT-3' 1-404=SEQ ID NO: 23) and 5'-CTGCA ACTCA AGCTT AAGCT CTCAT TGCGC GCAT-3' (I-402=SEQ ID NO: 24) were synthesized. I-404 corresponds to the first 6 amino acid triplets of the ATPase gene and upstream contains an Ecor1 coli site ("sense" DNA oligonucleotide) I-402 corresponds to the last 6 amino acid triplets and downstream contains a TAA stop codon and a Hind3 site ("antisense" DNA oligonucleotide). The region from pRH439 (1.3) coding for the HP-ATPase was amplified using these DNA oligonucleotides by means of polymerase chain reaction (PCR). The PCR product was cleaved with EcoR1 and Hind3 in order to release the cloning ends, and purified on an agarose gel. pTI2-1 was digested using the same enzyme combination (EcoR1 and Hind3). Plasmid and PCR products were ligated and cloned after transformation in E. coli MM294. The cloning product is plasmid PY25. The DNA sequence of the inserted ATPase gene was verified by means of DNA sequencing. The recombinant E. coli strain is called E. coli PY25. In E. coli PY25, the HP-ATPase gene is under the control of the tac promoter. The structure of the vector PY25 is indicated in FIG. 5.

3.1.3. Measuring device for determination of the metabolic activity of E. coli PY25

With the aid of a cytosensor microphysiometer (Molecular Devices, Gräfelfing), it is possible to measure and distinguish the metabolic activity of cells by means of their acidification rate. The acidification rate is defined as the rate at which the medium is acidified by the cellular metabolic activity. The biological working principle of the cytosensor is based on the fact that the H$^+$ concentration in the immediate environment of living cells depends on the metabolic activity. The cytosensor is based on a light-controlled sensor (silicon chip) which acts as a highly sensitive and rapid pH detector. The sensor is in direct contact with the measuring chamber in which the cells are incubated under a manipulable flow of medium. A voltage is applied via the sensor, the current flow being dependent on the proton coating of the oxynitride layer of the silicon chip (McConnel et al., Science 257,1906–1912, 1992). The sensor detects the smallest metabolic changes of cells which are located in the measurement or sensor chamber. The addition of media, nutrients and test substances is controlled via a computer-controlled system. Eight samples can be measured in parallel.

3.2. Measurement of the metabolic activity 3.2.1. Cytosensor experimental medium The experiments in the cytosensor were carried out in BSSGG medium. In this connection, BSS stands for "balanced salt solution", a weakly phosphate-buffered ion solution, and GG for the addition of glucose and glutamine as a nutrient and energy source.

BSSGG composition (pH 7.4)

138 mM NaCl 5 mM KCl 0.81 mM Na$_2$HPO$_4$ 0.11 mM NaH$_2$PO$_4$ 1.3 mM CaCl$_2$ 0.5 mM MgCl$_2$ 10 mM glucose 1 mM glutamine (NH$_4$)$_2$SO$_4$ is additionally added to the medium as a source of ammonium ions and sulfur (final concentration 10 mM).

3.2.2. Preparation of cells

M9 minimal medium (Molecular Cloning, Maniatis et al., Cold Spring Harbor Laboratory Press, 1989) is inoculated with recombinant E. coli and incubated at 37° C. overnight in a shaking incubator. The recombinant strain is E. coli PY25. The control strain employed is E. coli PTI2-1, which carries the plasmid without the insertion of the ATPase ("empty vector").

On the next day, 70 μl of cell suspension were mixed with 30 μl of molten agarose (Molecular Devices) and 10 μl each were spotted onto the membrane of an insert for the cytosensor measurement chamber. To harden the agarose, the inserts were incubated at +4° C. for 20–40 min and then transferred into the sensor chambers of the cytosensor according to the instructions of the manufacturer. The medium used was BSSGG.

3.2.3. Preparation of the cytosensor

The measuring chambers of the cytosensor were flooded with BSSGG at 50% pump power before inserting the sensor chambers with the cells. After 10 min, the prepared sensor chambers with the agarose-fixed cells were inserted. The following parameters were defined:

Temperature measuring chamber: 37° debubblers Δ: 6° C.

Pump and measuring cycle

| | pump phase | | |
|---|---|---|---|
| | Start | Stop | Speed |
| 1st interval | 00:00:00 (h:min:s) | 00:00:40 | 30% |
| rate measurement (measurement of the acidification or basification rate) | | | |
| | Start | Stop | |
| | 00:00:43 | 00:00:58 | |

The pump stops during the measuring phase (Speed=0%). total cycle: 00:01:00

Calibration of the apparatus follows, i.e. the calibration of the sensor chambers with respect to the activity of the cells employed on the basis of the set parameters. Further progress of the experiment takes place exactly according to the instructions of the manufacturer. Raw and rate data are recorded and stored. The rate data show the change in course of the cellular activity during the measuring phases (rate measurements). Here it can be read off to what extent induced changes in the metabolism of the cells occur which lead to changes in the surface charge on the oxynitride layer of the sensor. The rate data are indicated in –μVolt/s.

3.2.4. Carrying-out of experiments 3.2.4.1. Measurement of the activity of E. coli PY25 and E. coli PTI2-1

Influence on the HP-ATPase activity

FIG. 6 shows the rate data of the two recombinant E. coli strains E. coli PY25 (with HP-ATPase) and PTI2-1 (without HP-ATPase) in BSSGG supplemented with 10 mm (NH$_4$)$_2$SO$_4$. Both strains initially show a marked acidification behavior. E. coli PY25 is shown in measuring channel F, strain PTI2-1 in measuring channel B. On addition of the inducer isopropylthiogalactoside (IPTG, final concentration 1 μM) for the activation of the tac promoter, in this example both strains are at a rate of about –800 μVolt/s. Approximately 5 min after addition of IPTG, only E. coli PY25 shows a drastically falling acidification rate, which is about 100 μVolt/s in the minimum and is thus equivalent to a slight basification. The delayed action of the IPTG induction can be explained by the biosynthesis of the HP-ATPase which initially takes place.

The drop in the acidification rate of E. coli PY25 under these experimental conditions can only be observed in the presence of NH$_4$$^+$. If tetracycline, an inhibitor of bacterial protein biosynthesis, is added to the medium simultaneously with IPTG, no change in the metabolic activity of strain PY25 occurs.

3.2.4.2. Inhibition of the IPTG effect by ortho-vanadate

It is known that ortho-vanadate inhibits P-type ATPases in the lower μ-molar concentration range. FIG. 7 shows this inhibitory effect. The acidification rate of E. coli PY25 was initially recorded in the cytosensor in BSSGG supplemented with 10 mM (NH$_4$)$_2$SO$_4$ (measuring chambers F, G, H). In F and H, the cells were in this case exposed to vanadate at a final concentration of 10 μM. G contained no inhibitor. After 3.5 hours, preincubation is switched to BSSGG 10 mM (NH$_4$)$_2$SO$_4$ with 1 μM IPTG. In this case, 10 μM vanadate is additionally present in G (previously without vanadate), as well as in H (present before induction). In F, no vanadate is present with induction, but was present in the preincubation medium. As can be seen in FIG. 7, the induced inhibition of the acidification only occurs in sample G. Samples H and F, which contained an initial introduction of 10 μM vanadate, are not inhibited, i.e. the acidification rate does not decrease significantly in contrast to sample G.

This experimental structure shows the action of the vanadate as an inhibitor of the induced P-type ATPase and shows that the recombinant E. coli on this basis makes possible a screening for substances which interact with the expressed ATPase activity.

DESCRIPTION OF FIGURES

FIGS. 2a–e show the DNA sequence of the complete pRH439 Xho-EcoR1 insert (including SEQ ID NO: 1) and the derived ORF (open reading frame) of HP-ATPase. The DNA sequence starts with the C of the Xho1 (CTCGAG) recognition site in position 1 and ends with the C of the EcoR1 (GAATTC) restriction site in position 3411. The ORF which codes for an H. pylori P-type ATPase having 686 amino acids lies between position 1219 with the A of the ATG start codon and position 3276 with the T of the GCT alanine codon. A TAA follows on the ORF as a stop codon for the translation. The aforesaid amino acid sequence is indicated below the DNA sequence. The consensus sequence, which contains the phosphorylation site (Asp-388), is underlined.

FIGS. 3a–f show the DNA sequence of the complete pRH514 EcoR1-Xho1 insert and the derived amino acid sequence of the complete ORF. Amino acid sequences are indicated in the single letter code under the coding region. The complete, 5'-situated ORF encodes a protein of 506 amino acids with significant homology to bacterial response regulators. pRH514 overlaps with the DNA clone pRH439, which carries the gene for a P-type ATPase. pRH514 has the 5'-part of the ATPase gene 439. As the complete ORF of pRH514 of the ATPase is placed in front, the response regulator protein encoded on pRH514 was described as ATPase Associated Protein (AAP).

Figure 4D:
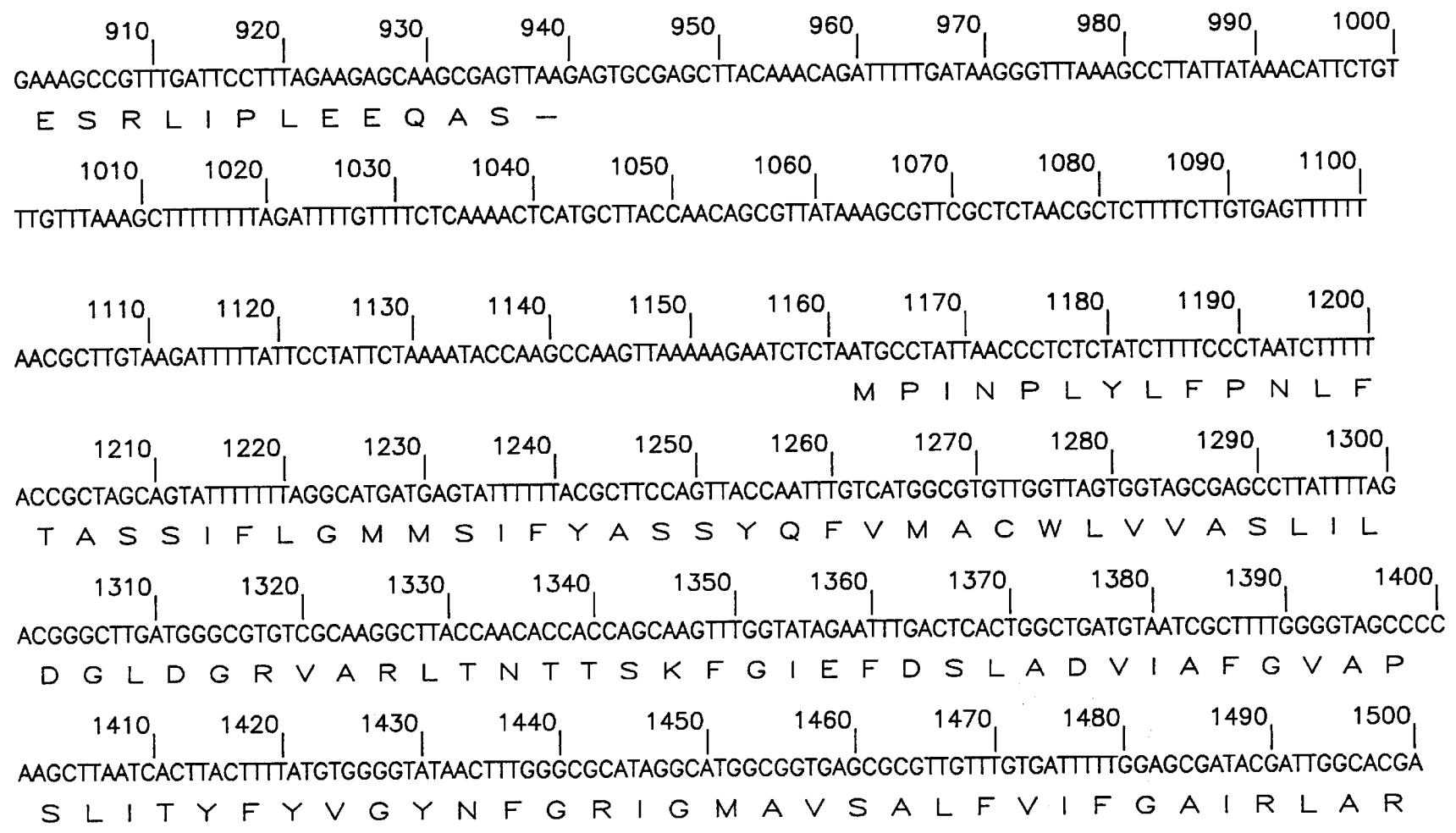

FIGS. 4a–i show the complete DNA insertion sequence (SEQ ID NO: 3) of the DNA clone pRH948 from the H. pylori gene bank. The terminal nucleotides, which are emphasized by underlining, further correlate with vector DNA. The nonunderlined DNA sequence represents the cloned Helicobacter DNA of plasmid pRH948. The H. pylori-specific DNA sequence comprises a total of 6 ORFs. Of these, the two outer ones are incomplete, since these are present interrupted by the cloning positions and thus change into the vector DNA sequence. The derived amino acid sequences are indicated under the DNA sequence in the single letter code, all 6 ORFs being taken into account. The position, nature and condition of the ORFs are described in the text. ORF 4 codes for the P-type ATPase 948.

FIG. 5 Plasmid maps of PY-25. The base vector is pTI2-1. This contains a tac promoter (P<TAC>), an ampicillin resistance gene (AP<R>) and a lacI$^Q$ gene (LACIQ), which expresses the lac repressor. Behind the tac promoter, the P-type ATPase gene (ATPASE) from pRH439 is cloned by means of EcoRI/HindIII restriction sites. The vector is suitable for the functional expression of Helicobacter genes in E. coli. The localization of the singular cleavage sites of EcoRI, Hind3 and Pst1 present are indicated.

FIG. 6 shows the acidification rates obtained for the expression of HP-ATPase in recombinant E. coli. The sensor chamber B contains recombinant E. coli with plasmid pTI2-1 as control vector. The sensor chamber F contains recombinant E. coli with the plasmid PY25 with inserted HP-ATPase gene. The cells were incubated as described under 5.2.4.1. After two hours, IPTG was added to the medium. In the presence of plasmid PY25 the acidification rate of E. coli is greatly decreased.

FIG. 7 shows the effect of ortho-vanadate on the acidification rate. The sensor chambers F, G and H contain E. coli with plasmid PY25. In the chambers F and H ortho-vanadate was added to the medium before induction with IPTG. After 3.5 hours IPTG (F) or IPTG was added to the medium in the presence of 10 μM ortho-vanadate. In cells which were preincubated with ortho-vanadate (F, H), the reduction of the acidification rate induced by IPTG was not observed.

Figure 1:
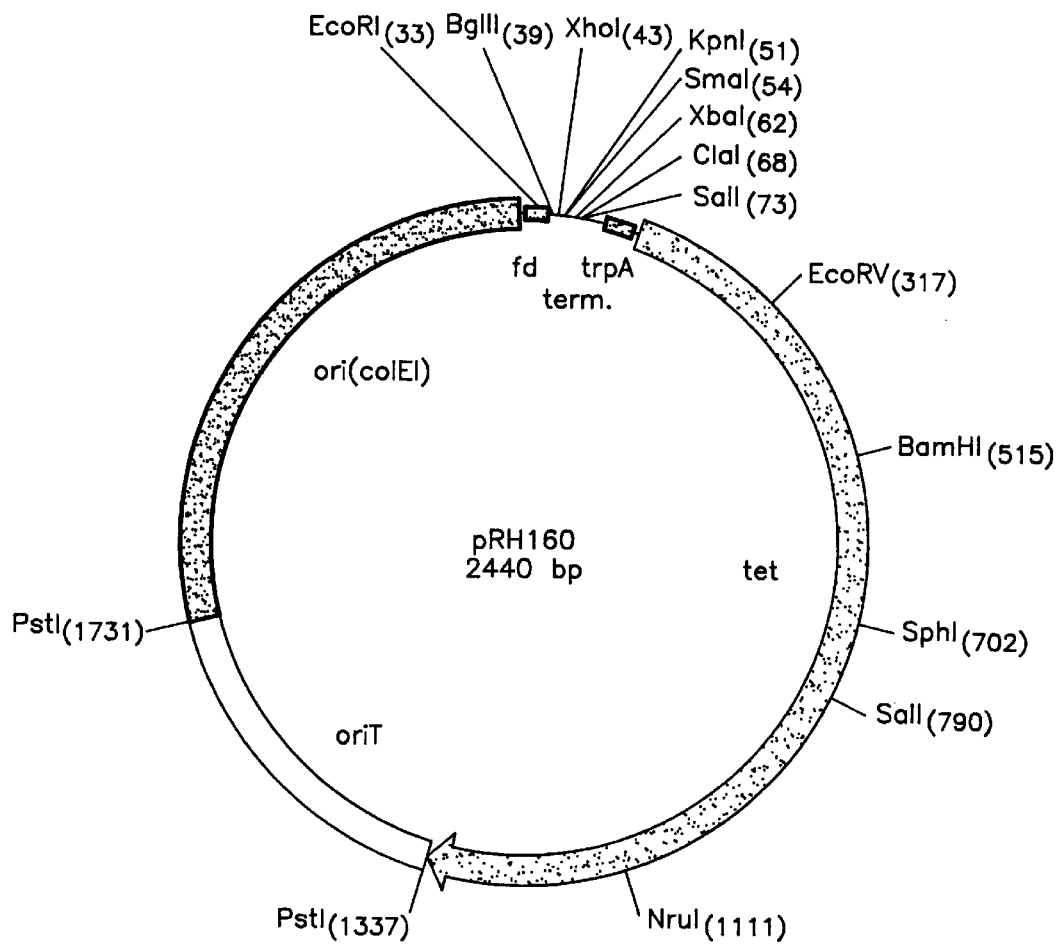
FIG. 1 represents the plasmid map of pRH160. The plasmid contains a tetracycline resistance marker gene. The position of the restriction sites for EcoR1, BglII, Xho1, Kpn1, Sma1, Xba1, Cla1, Sal1, EcoRv, BamH1, SpH1, Nru1 and Pst1 is indicated. The DNA fragments obtained by partial digestion of genomic H. pylori DNA with Sau3A were cloned in the BglII restriction position of the plasmid.

We claim:

1. A screening kit for the determination of the action of substances inhibiting the P-type ATPase activity of Helicobacter, comprising
   a) a recombinant organism consisting of host cells transformed using at least one Helicobacter P-type ATPase gene coding for a Helicobacter P-type ATPase according to SEQ ID No. 4 or SEQ ID No. 9 and controllable via a promoter,
   b) an inducer for the genetic activation of the P-type ATPase gene of a),
   c) cations which impair the metabolic activity of the recombinant organism only in the presence of Helicobacter P-type ATPase, and
   d) a measuring device for the determination of the metabolic activity of the recombinant organism.

2. A screening kit as claimed in claim 1, wherein the host cells are E. coli cells.

3. The screening kit as claimed in claim 2, wherein the host cells are E. coli K12 derivatives.

4. A screening kit as claimed in claim 3, wherein the E. coli K12 derivative is E. coli MM 294.

5. A screening kit as claimed in claim 1, wherein the promoter is a tac, Trc or Trp promoter.

6. A screening kit as claimed in claim 5, wherein the inducer is IPTG (isopropylthiogalactoside) in the case of tac and Trc promoters and β-IAA (indoleacetic acid) in the case of Trp promoters.

7. A screening kit as claimed in claim 1, wherein the cations are ammonium ions.

8. The screening kit as claimed in claim 1, further comprising an energy and/or nutrient source.

9. The screening kit as claimed in claim 8, further comprising an amino acid, and/or glucose.

10. A screening kit as claimed claim in claim 9, wherein the amino acid is glutamine.

11. A screening kit as claimed in claim 1, wherein the measuring device for the determination of the metabolic activity is a cytosensor microphysiometer.

12. A screening kit according to claim 1, wherein the Helicobacter P-type ATPase gene comprises a nucleotide sequence consisting of nucleotides 1219 to 3276 of SEQ ID No. 1 or a nucleotide sequence consisting of nucleotides 1872 to 4094 of SEQ ID No 3.

13. A process for screening an inhibitor of P-type ATPases of Helicobacter, wherein the metabolic activity of a recombinant host cell that, upon induction, expresses at least one Helicobacter ATPase according to SEQ ID No. 4 or SEQ ID No. 9 is determined in the presence of cations that impair the metabolic activity of said recombinant host cell only upon expression of said Helicobacter APTase.

14. A process as claimed in claim 13, wherein said metabolic activity is determined before and after induction of the Helicobacter ATPase.

15. A purified and isolated DNA sequence which codes for the Helicobacter-specific ATPase 439 according to SEQ ID No. 4.

16. A purified and isolated DNA sequence as claimed in claim 14 comprising a nucleotide sequence consisting of nucleotides 1219 to 3276 of SEQ ID No. 1.

17. A purified and isolated DNA sequence which codes for the Helicobacter-specific ATPase associated proteins 514 according to SEQ ID No. 5.

18. A purified and isolated DNA sequence as claimed in claim 17 comprising a nucleotide sequence consisting of nucleotides 115 to 1632 of SEQ ID No. 2.

19. A purified and isolated DNA sequence to which codes for the Helicobacter-specific ATPase 948 according to SEQ ID No. 9.

20. A purified and isolated DNA sequence as claimed in claim 13 comprising a nucleotide sequence consisting of nucleotides 1872 to 4094 of SEQ ID No. 3.

21. A vector containing a DNA sequence which codes for Helicobacter-specific ATPase 439 according to SEQ ID No. 4.

22. A vector as claimed in claim 21, wherein the DNA sequence comprises a nucleotide sequence consisting of nucleotides 1219 to 3276 of SEQ ID No. 1.

23. A vector containing a DNA sequence which codes for Helicobacter-specific ATPase associated Protein 514 according to SEQ ID No. 5.

24. A vector as claimed in claim 23, wherein the DNA sequence comprises a nucleotide sequence consisting of nucleotides 115 to 1632 of SEQ ID No. 2.

25. A vector containing a DNA sequence which codes for Helicobacter-specific ATPase 948 according to SEQ ID No. 9.

26. A vector as claimed in claim 25, wherein the DNA sequence comprises a nucleotide sequence consisting of nucleotides 1872 to 4094 of SEQ ID No. 3.

* * * * *

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 3411 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Helicobycter pylori
      (B) STRAIN: Helicobacter pylori 69A (C) INDIVIDUAL ISOLATE: Clinical isolate 69A (vii) IMMEDIATE SOURCE:
    (A) LIBRARY: Helicobacter pylori 69A - gene library in
        vector pRH160
    (B) CLONE: pRH439

(xi) SEQUENCE DESCRIPTION: SEQ ID NO: 1:

```
CTCGAGATCA AACCCAATCC TAACATTTTC CCCATGCTTT TAGACATTGC CATCAAACAC      60

CCCCATGCTA AAGTCATTGC GCCTAAGGCT AATGAAGAGC TTTTTTCGCT CATCCCTAAT     120

TTGCAATGCT TTTTTGTGGA GCATTTTAAA GAAGCGTTAG AAATCTTACA AAACCCTGAA     180

ATCAAAGCAG ACACCCACAC GAAAAAACTA CCCTTTAAAA CGATAGAATT GAACGATAAA     240

GAGTATTATT TTTCAGACGC CTATGCATTA GATTTTAAAG AAGTTAAGGG GCAAGCTGTC     300

GCTAAAGAAG CCGCTTTGAT CGCTAGCGCT GGGTTTCATA ACTTGATTTT AGAGGGAAGT     360

CCAGGGTGTG GGAAAAGCAT GATCATTAAT CGCATGCGTT ATATTTTACC TCCCTTAAGC     420

CTGAATGAAA TCCTAGAAGC GACAAAATTA CGCATTTTAA GCGAACAAGA CAGCGCCTAT     480

TACCCCTTAA GGAGTTTTAG AAACCCTCAC CAAAGCGCTT CAAAATCCAG CATTTTAGGC     540

TCAAGCTCTC TAAAAGAGCC AAAACCCGGC GAAATCGCCG TAGCGCATAA CGGCATGCTT     600

TTTTTTGATG AATTGCCTCA TTTTAAAAAG GAAATTTTGG AAGCTTTAAG AGAGCCTTTA     660

GAAAACAATA AATTGGTGGT TCACGAGTG CATAGCAAAA TTGAATACGA AACCTCTTTT     720

TTATTTGTGG GGGCTCAAAA CCCTTGCTTG TGTGGGAATT TACTCAGTGC GACCAAAGCA     780

TGCCGTTGCC AAGACAGAGA ATCACGCAG TATAAAAACC GCTTGAGCGA GCCTTTTTTA     840

GATAGGATTG ATTTGTTTGT GCAAATGGAA GAGGGGAATT ATAAAGACAC GCCGTCGCAT     900

TCTTGGACTT CAAAAGAGAT GCATCAATTA GTATTATTAG CTTTCAAACA GCAAAAATTA     960

AGGAAACAGA GCGTTTTTAA TGGTAAGCTT AATGAAGAGC AGATAGAACG ATTTTGCCCT    1020

TTAAACGCTG AAGCAAAAAA GTTGTTAGAG CAGGCGGTTG AAAGGTTTAA TCTGTCCATG    1080

CGCTCTGTTA ATAAGGTCAA AAAGGTCGCC AGGACGATTG CGGATTTAAA CGCTTGCGAG    1140

AATATAGAAA AATCTCACAT GCTTAAAGCG CTGAGTTTTA GAAAGATTTC TTAAAAGGAT    1200

TTTTATAAGG GAGAGAAAAT GCAAGAATAC CACATTCATA ATTTGGATTG CCCTGATTGC    1260

GCGTCTAAAT TGGAAAGGGA TTTAAACAAA CTAGACTATG TGAAAAAAGC TCAAATCAAT    1320

TTCAGCACCA GCAGGTTGTT TTTGGACACG AGCGATTTTG AAAAAGTTAA GGCTTTTATC    1380

AAGCAGAATG AACCGCATTT GAGCCTGTCT TTTAAAGAGG CCGCAGAAAA GCCCTTGAGT    1440

TTTACGCCAC TCATTGTTAC GATCGCTGTC TTTTTAGGCG CGATTTTAAT CTTACACCTA    1500

AACCCTAGCC CTTTGATTGA AAAGGCTATG TTTTTCGTGT TGGCTTTGGT GTATCTAGTG    1560

AGCGGTAAAG ATGTGATTTT AGGGGCGTTT CGTGGGCTTA GGAAAGGGCA GTTTTTTGAT    1620

GAAAACGCTT TGATGCTCAT TGCGACTATT GCGGCTTTTT GCGTGGGGGC TTATGAAGAG    1680

AGCGTGTCTA TTATGGTGTT TTATTCAGCG GGCGAATTTT TGCAAAAACT CGCTATCGCT    1740

CGCTCTAAAA AATCCCTTAA GGCTTTAGTG GATGTCGCTC CTAATTGGC TTATTTGAAA     1800

AAGGGCGATG CGTTAGTGAG CGTTGCGCCT GAAGATTAA GAATTAATGA CATTGTGGTG    1860

GTGAAAGTCG GCGAAAAAGT GCCTGTGGAT GGCGTGGTGA TTAAGGGCGA AAGTTTGCTA    1920

GATGAAAGGG CGTTGAGCGG GGAGTCTATG CCGGTTAATG TCAGCGAACG CTCTAAAGTT    1980

TTAGGGGGGA GCTTGAATTT AAAAGCGGTC CTTGAAATTC AAGTAGAGAA AATGTATAAA    2040

GATTCTTCTA TCGCTAAAGT GGTAGATTTG GTCCAACAAG CCACGAATGA AAAGAGCGAA    2100

ACCGAGAAAT TTATCACTAA ATTTTCACGC TACTACACCC CAAGCGTTTT ATTCATTGCG    2160
```

```
TTAATGATTG CTGTATTACC GCCCTTATTT TCTATGGGGA GCTTTGATGA GTGGATTTAT     2220

AGGGGGCTTG TGGCTTTAAT GGTGAGCTGC CCTTGCGCGT TAGTGATTTC TGTGCCTTTA     2280

GGGTATTTTG GAGGCGTGGG AGCGGCGAGC CGAAAGGGTA TTTTAATGAA AGGCGTGCAT     2340

GTTTTAGAAG TGCTTACCCA AGCTAAAAGC ATCGCCTTTG ATAAAACCGG CACTTTGACT     2400

AAAGGCGTTT TTAAAGTAAC AGATATTGTG CCGCAAAACG GGCATTCTAA GAAGAAGTT     2460

TTGCATTACG CTTCTTGTTC GCAGCTCTTA TCCACGCACC CTATCGCTTT ATCCATTCAA     2520

GAAGCATGCG AAGAAATGTT AAAGGACGAC AAGCACCAGC ATGACATTAA AAATTACGAA     2580

GAATTGAGCG GAATGGGGGT TAAAGCGCAA TGCCATACGG ATTTAATCAT CGCAGGGAAT     2640

GAAAAAATGC TGGATCAATT CCATATCGCG CACAGCCCTT CCAAAGAAAA CGGCACGATC     2700

GTGCATGTGG CTTTCAACCA AACTTATATA GGCTATATCG TCATTAGCGA TGAGATTAAA     2760

GATGACGCCA TAGAGTGCTT AAGGGATTTA AAAGCGCAAG GGATAGAAAA TTTTTGCATT     2820

TTGAGCGGGG ACAGAAAAAG CGCGACTGAG AGCATCGCTC AAACTCTGGG CTGTGAATAT     2880

TATGCGAGTT TGTTGCCTGA AGAAAAAACG AGCGTGTTTA AAACTTTTAA AGAACGCTAT     2940

AAAGCCCCGG CGATTTTTGT AGGCGATGGT ATCAATGACG CTCCGACTCT AGCGAGCGCT     3000

GATGTGGGGA TTGGCATGGG GAAAGGCTCA GAATTGAGCA AGCAAAGCGC GGACATTGTG     3060

ATCACCAATG ACTCCTTAAA TTCGTTAGTG AAAGTTTTAG CGATCGCTAA AAAAACTAAA     3120

AGCATTATTT GGCAAAATAT CTTGTTCGCT TTGGGGATTA AAGCCGTTTT TATCGTGCTA     3180

GGGCTTATGG GGGTAGCGAG CTTGTGGGAA GCGGTCTTTG GCGATGTGGG GGTTACGCTT     3240

TTAGCCTTAG CCAACTCCAT GCGCGCAATG AGAGCTTAAA GCCTTGAATC CATCATCAAA     3300

GAGCTAGAAG GGGGGCAAAA TGAACCACAT AGAAAAACTA CTCCAAACCT TAGCGCCTAA     3360

AGGGGTGGAG TTTAGGAAGT TGGGGAGGT GCTAGAATAT GATCTGAATT C              3411

(2) INFORMATION FOR SEQ ID NO: 2:

(i) SEQUENCE CHARACTERISTICS:
        (A) LENGTH: 3097 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Helicobacter pylori
         (B) STRAIN: Helicobacter pylori 69A
         (C) INDIVIDUAL ISOLATE: Clinical isolate 69A (vii) IMMEDIATE SOURCE:
          (A) LIBRARY: Helicobacter pylori 69A - gene library in
              vector pRH160
          (B) CLONE: pRH514

(xi) SEQUENCE DESCRIPTION: SEQ ID NO: 2:

GATCGATCAT CTCAATGGCG TGTTATTCGT GGATAAATTA TCCATTTTGA AGCGTAAGAA       60

ATTTGAAAAA GAATTAAAAG AATTAAGTAA AAATCCCAGA AACAAGTCTT AATCATGATT      120

AACACGATAT TTTGCGCGAC CATGCAAAGG GGAGTGGCAG AAATCGTGGC TGTAGAAGCG      180

ACTTTCACAA GGGCTTTGCC GGCGTTTGTG ATTTCAGGCT TGGCTAATAG CTCTATCCAA      240

GAAGCCAAAC AGCGGGTCCA ATCGGCTTTA CAAAATAACG ATTTCACTTT CCCGCCTTTA      300
```

```
AAAATCACCA TCAACCTTTC CCCTTCAGAT TTGCCTAAAT CCGGGAGCCA TTTTGATTTG      360

CCTATCGCTC TTTTAATCGC TTTGCAAAAA CAAGAGTTGG CTTTTAAAGA GTGGTTTGCT      420

TTTGGGGAGT TAGGGCTTGA TGGCAAGATC AAACCCAATC CTAACATTTT CCCCATGCTT      480

TTAGACATTG CCATCAAACA CCCCCATGCT AAAGTCATTG CGCCTAAGGC TAATGAAGAG      540

CTTTTTTCGC TCATCCCTAA TTTGCAATGC TTTTTTGTGG AGCATTTTAA AGAAGCGTTA      600

GAAATCTTAC AAAACCCTGA AATCAAAGCA GACACCCACA CGAAAAAACT ACCCTTTAAA      660

ACGATAGAAT TGAACGATAA AGAGTATTAT TTTTCAGACG CCTATGCATT AGATTTTAAA      720

GAAGTTAAGG GGCAAGCTGT CGCTAAAGAA GCCGCTTTGA TCGCTAGCGC TGGGTTTCAT      780

AACTTGATTT TAGAGGGAAG TCCAGGGTGT GGGAAAAGCA TGATCATTAA TCGCATGCGT      840

TATATTTTAC CTCCCTTAAG CCTGAATGAA ATCCTAGAAG CGACAAAATT ACGCATTTTA      900

AGCGAACAAG ACAGCGCCTA TTACCCCTTA AGGAGTTTTA GAAACCCTCA CCAAAGCGCT      960

TCAAAATCCA GCATTTTAGG CTCAAGCTCT CTAAAAGAGC AAAACCCGG CGAAATCGCC     1020

GTAGCGCATA ACGGCATGCT TTTTTTTGAT GAATTGCCTC ATTTTAAAAA GGAAATTTTG     1080

GAAGCTTTAA GAGAGCCTTT AGAAAACAAT AAATTGGTGG TTTCACGAGT GCATAGCAAA     1140

ATTGAATACG AAACCTCTTT TTTATTTGTG GGGGCTCAAA ACCCTTGCTT GTGTGGGAAT     1200

TTACTCAGTG CGACCAAAGC ATGCCGTTGC CAAGACAGAG AAATCACGCA GTATAAAAAC     1260

CGCTTGAGCG AGCCTTTTTT AGATAGGATT GATTTGTTTG TGCAAATGGA AGAGGGGAAT     1320

TATAAAGACA CGCCGTCGCA TTCTTGGACT TCAAAAGAGA TGCATCAATT AGTATTATTA     1380

GCTTTCAAAC AGCAAAAATT AAGGAAACAG AGCGTTTTTA ATGGTAAGCT TAATGAAGAG     1440

CAGATAGAAC GATTTTGCCC TTTAAACGCT GAAGCAAAAA AGTTGTTAGA GCAGGCGGTT     1500

GAAAGGTTTA ATCTGTCCAT GCGCTCTGTT AATAAGGTCA AAAGGTCGC CAGGACGATT      1560

GCGGATTTAA ACGCTTGCGA GAATATAGAA AAATCTCACA TGCTTAAAGC GCTGAGTTTT     1620

AGAAAGATTT CTTAAAAGGA TTTTTATAAG GGAGAGAAAA TGCAAGAATA CCACATTCAT     1680

AATTTGGATT GCCCTGATTG CGCGTCTAAA TTGGAAAGGG ATTTAAACAA ACTAGACTAT     1740

GTGAAAAAAG CTCAAATCAA TTTCAGCACC AGCAGGTTGT TTTTGGACAC GAGCGATTTT     1800

GAAAAAGTTA AGGCTTTTAT CAAGCAGAAT GAACCGCATT TGAGCCTGTC TTTTAAAGAG     1860

GCCGCAGAAA AGCCCTTGAG TTTTACGCCA CTCATTGTTA CGATCGCTGT CTTTTTAGGC     1920

GCGATTTTAA TCTTACACCT AAACCCTAGC CCTTTGATTG AAAAGGCTAT GTTTTTCGTG     1980

TTGGCTTTGG TGTATCTAGT GAGCGGTAAA GATGTGATTT TAGGGCGTT TCGTGGGCTT      2040

AGGAAAGGGC AGTTTTTTGA TGAAAACGCT TTGATGCTCA TTGCGACTAT TGCGGCTTTT     2100

TGCGTGGGGG CTTATGAAGA GAGCGTGTCT ATTATGGTGT TTTATTCAGC GGGCGAATTT     2160

TTGCAAAAAC TCGCTATCGC TCGCTCTAAA AAATCCCTTA AGGCTTTAGT GGATGTCGCT     2220

CCTAATTTGG CTTATTTGAA AAAGGGCGAT GCGTTAGTGA GCGTTGCGCC TGAAGATTTA     2280

AGAATTAATG ACATTGTGGT GGTGAAAGTC GGCGAAAAAG TGCCTGTGGA TGGCGTGGTG     2340

ATTAAGGGCG AAAGTTTGCT AGATGAAAGG GCGTTGAGCG GGGAGTCTAT GCCGGTTAAT     2400

GTCAGCGAAC GCTCTAAAGT TTTAGGGGGG AGCTTGAATT TAAAAGCGGT CCTTGAAATT     2460

CAAGTAGAGA AAATGTATAA AGATTCTTCT ATCGCTAAAG TGGTAGATTT GGTCCAACAA     2520

GCCACGAATG AAAAGAGCGA AACCGAGAAA TTTATCACTA AATTTTCACG CTACTACACC     2580

CCAAGCGTTT TATTCATTGC GTTAATGATT GCTGTATTAC CGCCCTTATT TTCTATGGGG     2640

AGCTTTGATG AGTGGATTTA TAGGGGCTT GTGGCTTTAA TGGTGAGCTG CCCTTGCGCG      2700
```

-continued

| | |
|---|---|
| TTAGTGATTT CTGTGCCTTT AGGGTATTTT GGAGGCGTGG GAGCGGCGAG CCGAAAGGGT | 2760 |
| ATTTTAATGA AAGGCGTGCA TGTTTTAGAA GTGCTTACCC AAGCTAAAAG CATCGCCTTT | 2820 |
| GATAAAACCG GCACTTTGAC TAAAGGCGTT TTTAAAGTAA CAGATATTGT GCCGCAAAAC | 2880 |
| GGGCATTCTA AGAAGAAGT TTTGCATTAC GCTTCTTGTT CGCAGCTCTT ATCCACGCAC | 2940 |
| CCTATCGCTT TATCCATTCA AGAAGCATGC GAAGAAATGT TAAGGACGA CAAGCACCAG | 3000 |
| CATGACATTA AAAATTACGA AGAATTGAGC GGAATGGGGG TTAAAGCGCA ATGCCATACG | 3060 |
| GATTTAATCA TCGCAGGGAA TGAAAAAATG CTGGATC | 3097 |

(2) INFORMATION FOR SEQ ID NO: 3:

(i) SEQUENCE CHARACTERISTICS:
        (A) LENGTH: 4495 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Helicobacter pylori
        (B) STRAIN: Helicobacter pylori 69A
        (C) INDIVIDUAL ISOLATE: Clinical isolate 69A (vii) IMMEDIATE SOURCE:
        (A) LIBRARY: Helicobacter pylori 69A - gene library in
            vector pRH160
        (B) CLONE: pRH948

(xi) SEQUENCE DESCRIPTION: SEQ ID NO: 3:

| | |
|---|---|
| TTGAATTCAG ATCCGGCCTT AATGCGTCCA GGGCGCTTTG ACAGGCAGGT TTTAGTGGAT | 60 |
| AAGCCTGATT TTAATGGCAG AGTAGAAATC TTAAAAGTGC ATATTAAAGG CGTGAAACTC | 120 |
| GCTAACGATG TGAATTTGCA AGAAGTCGCC AAACTCACCG CAGGGCTTGC AGGAGCGGAT | 180 |
| TTAGCGAATA TCATCAATGA AGCCGCGCTT TTAGCAGGAA GAAACAACCA AAAAGAAGTC | 240 |
| AGGCAACAGC ATTTAAAAGA AGCGGTTGAA AGAGGGATTG CGGGGTTAGA AAAGAAAAGC | 300 |
| AGGCGCATCA GTCCTAAGGA AAAGAAAATC GTCGCCTACC ATGAAAGCGG GCATGCCGTG | 360 |
| ATTTCTGAAA TGACTAAAGG GAGTGCTAGG GTGAATAAAG TTTCTATCAT TCCAAGGGGC | 420 |
| ATGGCGGCTT TAGGCTACAC CCTTAACACG CCTGAAGAAA ACAAATACTT GATGCAAAAA | 480 |
| CACGAACTCA TCGCTGAAAT TGATGTGCTT TTAGGCGGAA GAGCGGCTGA AGATGTCTTT | 540 |
| TTGGAAGAAA TTTCTACCGG TGCGAGCAAC GATTTAGAAA GAGCGACTGA TATTATTAAA | 600 |
| GGCATGGTGA GTTACTACGG CATGAGCAGT GTCAGTGGGC TTATGGTGTT AGAAAAGCAA | 660 |
| CGGAACGCCT TTTTAGGAGG CGGTTATGGA AGCAGTAGGG AATTTAGCGA AAAAACCGCA | 720 |
| GAAGAAATGG ATCTTTTCAT TAAAAACTTG CTAGAAGAGC GCTATGAGCA TGTCAAACAA | 780 |
| ACCTTGAGCG ACTACAGAGA AGCGATTGAA ATCATGGTCA AGAATTGTT TGACAAAGAA | 840 |
| GTCATTACAG GCGAAAGGGT GCGTGAAATC ATCAGCGAAT ACGAAGTTGC CAACAATTTA | 900 |
| GAAAGCCGTT TGATTCCTTT AGAAGAGCAA GCGAGTTAAG AGTGCGAGCT TACAAACAGA | 960 |
| TTTTTGATAA GGGTTTAAAG CCTTATTATA ACATTCTGT TTGTTAAAG CTTTTTTTTA | 1020 |
| GATTTTGTTT TCTCAAAACT CATGCTTACC AACAGCGTTA TAAAGCGTTC GCTCTAACGC | 1080 |
| TCTTTTCTTG TGAGTTTTTT AACGCTTGTA AGATTTTAT TCCTATTCTA AAATACCAAG | 1140 |
| CCAAGTTAAA AAGAATCTCT AATGCCTATT AACCCTCTCT ATCTTTTCCC TAATCTTTTT | 1200 |

```
ACCGCTAGCA GTATTTTTTT AGGCATGATG AGTATTTTTT ACGCTTCCAG TTACCAATTT      1260

GTCATGGCGT GTTGGTTAGT GGTAGCGAGC CTTATTTTAG ACGGGCTTGA TGGGCGTGTC      1320

GCAAGGCTTA CCAACACCAC CAGCAAGTTT GGTATAGAAT TTGACTCACT GGCTGATGTA      1380

ATCGCTTTTG GGGTAGCCCC AAGCTTAATC ACTTACTTTT ATGTGGGGTA TAACTTTGGG      1440

CGCATAGGCA TGGCGGTGAG CGCGTTGTTT GTGATTTTTG GAGCGATACG ATTGGCACGA      1500

TTCAATATCA GCACCAACAC AAGCGACCCC TATTCTTTTA TCGGTATCCC CATTCCTGCG      1560

GCGGCGGTAT TGGTGGTGCT TTGTGTGTTA TTGGATAACA AATACCATTT TTTAGAAGGA      1620

AATACCGAAA AGTTATTTTT AAGCTTTATT GTTTTATTGG GGGTGCTTAT GGTGAGCAAT      1680

ATCCGCTACC CTAATTTTAA AAAGTCAAA TGGAATCTCA AGCTTTTTAT CTTAGTGTTG      1740

ATTTTTTTAT CGTTAGTGTT TGTGCGCCCT TTAGAGGCTT AAGCGTGTT TATGGGGTTG      1800

TATTTGATTT ATGGCATCAT TCGGTGGCTT TTTTTAATGG TAAAAATTAT TTTTAATAAA      1860

AATAAAAGTG CATGAAAGAA TCTTTTTACA TAGAGGGAAT GACTTGCACG GCGTGTTCTA      1920

GCGGGATTGA ACGCTCTTTA GGGCGTAAGA GTTTTGTGAA AAAATAGAA GTGAGCCTTT      1980

TAAATAAGAG CGCTAACATT GAATTTAACG AAAATGAAAC CAATTTAGAC GAGATTTTTA      2040

AACTCATTGA AAAACTGGGT TATAGCCCTA AAAAACTCT AGCAGAAGAA AAAAAAGAAT      2100

TTTTTAGCCC TAATGTTAAA TTAGCGTTGG CGGTTATTTT CACGCTTTTT GTGGTGTATC      2160

TTTCTATGGG GGCGATGCTT AGTCCTAGCC TTTTACCTGA AAGCTTGCTT ACGATTAACA      2220

ACCATAGTAA TTTTTTAAAC GCATGCTTAC AGCTTATAGG CACGCTCATT GTCATGCATT      2280

TAGGGAGGGA TTTTTACATT CAAGGGTTTA AAGCCTTATG GCACAGACAA CCCAACATGA      2340

GTAGCCTTAT CGCCATAGGC ACAAGCGCTG CCTTAATCTC AAGCTTGTGG CAATTGTATT      2400

TCGTTTATAC AAGCCAGTGG TCTTATGGGC ATTATTATTT TGAAAGCGTG TGCGTGATTT      2460

TAATGTTTGT AATGGTGGGC AAACGCATTG AAAATGTTTC TAAAGACAAA GCTTTAGACG      2520

CTATGCAAGC CTTGATGAAA AACGCCCCAA AAACCGCCCT TAAAATGCAC AATAACCAAC      2580

AGATTGAAGT TTTAGTGGAT AGCATTGTGG TGGGGATAT TCTAAAGGTT CTCCCTGGAA       2640

GCGCGATTGC GGTGGATGGC GAAATCATAG AGGGCGAAGG GGAATTAGAT GAAAGCATGT      2700

TAAGCGGCGA AGCGTTGCCG GTTTATAAAA AGTCGGCGA TAAAGTCTTT TCAGGGACAT      2760

TCAATAGCCA CACGAGTTTT TTAATGAAAG CCACGCAAGA TAACAAAAAC AGCACCTTGT      2820

CTCAAATTGT AGAAATGATC CATAACGCTC AAAGCTCAAA GGCAGAGATT TCTCGCTTAG      2880

CGGATAAGGT TTCAAGCGTG TTTGTGCCAA GCGTGATCGC TATCGCTATT TTAGCGTTTG      2940

TGGTGTGGCT CATCATCGCG CCTAAACCCG ATTTTTGGTG GAATTTTGGA ATCGCTTTAG      3000

AAGTGTTTGT ATCGGTTTTA GTGATTTCTT GCCCTTGCGC TTTAGGATTG GCTACACCTA      3060

TGAGTATTTT AGTAGCGAAC CAAAAAGCGA GTTCTTTAGG TTTATTTTTT AAAGACGCTA      3120

AAAGTTTAGA AAAAGCAAGG CTAGTCAATA CGATCGTTTT TGATAAAACC GGCACGCTCA      3180

CTAACGGCAA GCCTGTCGTT AAAAGCGTTC ATTCTAACAT AGAATTATTA GAGTTATTGA      3240

GTTTAGCGGG CAGTATTGAA AAGAGCAGCG AACATGTCAT TGCTAAAGGG ATTGTAGAAT      3300

ACGCCAAAGA GCATAACGCT CCCTTAAAAG AAATGAGTGA AGTTAAAGTG AAAACGGGTT      3360

TTGGCATCAG CGCTAAAACA GATTATCAAG GCGCTAAAGA GGTTATCAAA GTCGGTAATA      3420

GCGAATTTTT TAACCCTATT AACGCACTAG AAATTCAAGA AAACGGGATT TTAGTGTTTG      3480

TGGGTAGAGT GATCAGTGAA AAAGAAGACG AGCTTTTAGG GGCGTTTGTT TTAGAAGATT      3540

TGCCCAAAAA AGGCGTGAAA GAGCATATCG CTCAAATCAA AAAATTAGGC ATTAACACTT      3600
```

```
TTCTTTTAAG CGGGGACAAT AGAGAGAATG TCAAAAAATG CGCGCTTGAA TTAGGGATTG    3660

ATGGTTATAT CAGCAACGCT AAACCACAAG ACAAGCTCAA CAAGATCAAA GAGCTTAAGG    3720

AAAAAGGGCA GATCGTTATG ATGGTAGGCG ATGGCTTGAA TGACGCTCCT AGCCTTGCTA    3780

TGAGCGATGT GGCAGTGGTG ATGGCTAAAG GGAGCGATGT GAGCGTGCAA GCAGCGGATA    3840

TTGTGAGCTT TAATAACGAC ATTAAATCGG TTTATAGCGC GATTAAATTG AGCCAAGCGA    3900

CCATCAAAAA TATCAAAGAA AATTTGTTTT GGGCTTTTTG TTATAATAGC GTGTTTATCC    3960

CTTTAGCTTG TGGGGTTCTT TATAAAGCTA ATATCATGTT AAGCCCGGCG ATTGCGGGTT    4020

TAGCGATGAG TTTAAGCTCT GTGAGTGTGG TCTTAAACTC CCAAAGGCTA AGGAATTTTA    4080

AAATTAAGGA TCATTGAATG AAAGTTACTT TTCAAGTGCC AAGCATTACT TGCAACCATT    4140

GCGTGGATAA AATTGAAAAA TTTGTGGGCG AAATTGAAGG TGTGAGCTTT ATTGATGCGA    4200

GCGTGGAAAA AAAGAGCGTG GTTGTAGAAT TTGACGCTCC AGCGACACAG GATTTGATTA    4260

AGGAAGCCTT ATTGGATGCG GGCAAGAAG TAATATAATA AAGGTGTGTG ATATAGAAGT    4320

ATCGGATTAA AAACCGCAAC ATTCAAAAGG GTTGTTATCT TTTAATTCTT GGGTTTGTTT    4380

GGGTATTTTC ACGCCCTTCA ATGGTGATTT ATCATAACCA TAAGAGAAAA AATTATCGTA    4440

TTTCCCCCTT TTCTTACTCC AATTTTTTAT ACATACGGAT CTCGAGGTAC CCGGG         4495
```

(2) INFORMATION FOR SEQ ID NO: 4:

(i) SEQUENCE CHARACTERISTICS:
        (A) LENGTH: 686 amino acids
        (B) TYPE: amino acid
        (C) STRANDEDNESS:
        (D) TOPOLOGY: linear (ii) MOLECULE TYPE: protein (iii) HYPOTHETICAL: YES (vi) ORIGINAL SOURCE:
        (A) ORGANISM: Helicobacter pylori
        (B) STRAIN: Helicobacter pylori 69A
        (C) INDIVIDUAL ISOLATE: Clinical isolate 69A (vii) IMMEDIATE SOURCE:
        (A) LIBRARY: Helicobacter pylori 69A - gene library in
            vector pRH160
        (B) CLONE: pRH439

(xi) SEQUENCE DESCRIPTION: SEQ ID NO: 4:

```
Met Gln Glu Tyr His Ile His Asn Leu Asp Cys Pro Asp Cys Ala Ser
1               5                  10                  15

Lys Leu Glu Arg Asp Leu Asn Glu Leu Asp Tyr Val Lys Lys Ala Gln
            20                  25                  30

Ile Asn Phe Ser Thr Ser Lys Leu Phe Leu Asp Thr Ser Asp Phe Glu
        35                  40                  45

Lys Val Lys Ala Phe Ile Lys Gln Asn Glu Pro His Leu Ser Leu Ser
    50                  55                  60

Phe Lys Glu Ala Thr Glu Lys Pro Leu Ser Phe Thr Pro Leu Ile Ile
65                  70                  75                  80

Thr Ile Met Val Phe Leu Gly Ala Ile Leu Ile Leu His Leu Asn Pro
                85                  90                  95

Ser Pro Leu Ile Glu Lys Ala Met Phe Phe Val Leu Ala Leu Val Tyr
            100                 105                 110

Leu Val Ser Gly Lys Asp Val Ile Leu Gly Ala Phe Arg Gly Leu Arg
        115                 120                 125
```

-continued

```
Lys Gly Gln Phe Phe Asp Glu Asn Ala Leu Met Leu Ile Ala Thr Ile
    130                 135                 140
Ala Ala Phe Phe Val Gly Ala Tyr Glu Glu Ser Val Ser Ile Met Val
145                 150                 155                 160
Phe Tyr Ser Ala Gly Glu Phe Leu Gln Lys Leu Ala Val Ser Arg Ser
                165                 170                 175
Lys Lys Ser Leu Lys Ala Leu Val Asp Val Ala Pro Asn Leu Ala Tyr
            180                 185                 190
Leu Lys Lys Gly Asp Glu Leu Val Ser Val Ala Pro Glu Asp Leu Arg
        195                 200                 205
Val Asn Asp Ile Val Val Lys Val Gly Glu Lys Val Pro Val Asp
    210                 215                 220
Gly Val Val Lys Gly Glu Ser Leu Leu Asp Glu Arg Ala Leu Ser
225                 230                 235                 240
Gly Glu Ser Met Pro Val Asn Val Ser Glu Asn Ser Lys Val Leu Gly
                245                 250                 255
Gly Ser Leu Asn Leu Lys Ala Val Leu Glu Ile Gln Val Glu Lys Met
            260                 265                 270
Tyr Lys Asp Ser Ser Ile Ala Lys Val Val Asp Leu Val Gln Gln Ala
        275                 280                 285
Thr Asn Glu Lys Ser Glu Thr Glu Lys Phe Ile Thr Lys Phe Ser Arg
    290                 295                 300
Tyr Tyr Thr Pro Ser Val Leu Phe Ile Ala Leu Met Ile Ala Val Leu
305                 310                 315                 320
Pro Pro Leu Phe Ser Met Gly Ser Phe Asp Glu Trp Ile Tyr Arg Gly
                325                 330                 335
Leu Val Ala Leu Met Val Ser Cys Pro Cys Ala Leu Val Ile Ser Val
            340                 345                 350
Pro Leu Gly Tyr Phe Gly Gly Val Gly Ala Ala Ser Arg Lys Gly Ile
        355                 360                 365
Leu Met Lys Gly Val His Val Leu Glu Val Leu Thr Gln Ala Lys Ser
    370                 375                 380
Ile Ala Phe Asp Lys Thr Gly Thr Leu Thr Lys Gly Val Phe Lys Val
385                 390                 395                 400
Thr Asp Ile Val Pro Gln Asn Gly His Ser Lys Glu Val Leu His
                405                 410                 415
Tyr Ala Ser Cys Ser Gln Leu Leu Ser Thr His Pro Ile Ala Leu Ser
            420                 425                 430
Ile Gln Lys Ala Cys Glu Glu Met Leu Lys Asp Asp Lys His Gln His
        435                 440                 445
Asp Ile Lys Asn Tyr Glu Glu Val Ser Gly Met Gly Val Lys Ala Gln
    450                 455                 460
Cys His Thr Asp Leu Ile Ile Ala Gly Asn Glu Lys Met Leu Asp Gln
465                 470                 475                 480
Phe His Ile Ala His Ser Pro Ser Lys Glu Asn Gly Thr Ile Val His
                485                 490                 495
Val Ala Phe Asn Gln Thr Tyr Val Gly Tyr Ile Val Ile Ser Asp Glu
            500                 505                 510
Ile Lys Asp Asp Ala Ile Glu Cys Leu Arg Asp Leu Lys Val Gln Gly
        515                 520                 525
Ile Glu Asn Phe Cys Ile Leu Ser Gly Asp Arg Lys Ser Ala Thr Glu
    530                 535                 540
Ser Ile Ala Gln Thr Leu Gly Cys Glu Tyr His Ala Ser Leu Leu Pro
545                 550                 555                 560
```

```
Glu Glu Lys Thr Ser Val Phe Lys Thr Phe Lys Glu Arg Tyr Lys Ala
            565                 570                 575

Pro Ala Ile Phe Val Gly Asp Gly Ile Asn Asp Ala Pro Thr Leu Ala
            580                 585                 590

Ser Ala Asp Val Gly Ile Gly Met Gly Lys Gly Ser Glu Leu Ser Lys
            595                 600                 605

Gln Ser Ala Asp Ile Val Ile Thr Asn Asp Ser Leu Asn Ser Leu Val
            610                 615                 620

Lys Val Leu Ala Ile Ala Lys Lys Thr Lys Ser Ile Ile Trp Gln Asn
625                 630                 635                 640

Ile Leu Phe Ala Leu Gly Ile Lys Ala Val Phe Ile Val Leu Gly Leu
            645                 650                 655

Met Gly Val Ala Ser Leu Trp Glu Ala Val Phe Gly Asp Val Gly Val
            660                 665                 670

Thr Leu Leu Ala Leu Ala Asn Ser Met Arg Ala Met Arg Ala
            675                 680                 685
```

(2) INFORMATION FOR SEQ ID NO: 5:

(i) SEQUENCE CHARACTERISTICS:
        (A) LENGTH: 506 amino acids
        (B) TYPE: amino acid
        (C) STRANDEDNESS:
        (D) TOPOLOGY: linear (ii) MOLECULE TYPE: protein (iii) HYPOTHETICAL: YES (vi) ORIGINAL SOURCE:
        (A) ORGANISM: Helicobacter pylori
        (B) STRAIN: Helicobacter pylori 69A
        (C) INDIVIDUAL ISOLATE: Clinical isolate 69A (vii) IMMEDIATE SOURCE:
        (A) LIBRARY: Helicobacter pylori 69A - gene library in
            vector pRH160
        (B) CLONE: pRH514

(xi) SEQUENCE DESCRIPTION: SEQ ID NO: 5:

```
Met Ile Asn Thr Ile Phe Cys Ala Thr Met Gln Arg Gly Val Ala Glu
1               5                   10                  15

Ile Val Ala Val Glu Ala Thr Phe Thr Arg Ala Leu Pro Ala Phe Val
            20                  25                  30

Ile Ser Gly Leu Ala Asn Ser Ser Ile Gln Glu Ala Lys Gln Arg Val
            35                  40                  45

Gln Ser Ala Leu Gln Asn Asn Asp Phe Thr Phe Pro Pro Leu Lys Ile
50                  55                  60

Thr Ile Asn Leu Ser Pro Ser Asp Leu Pro Lys Ser Gly Ser His Phe
65                  70                  75                  80

Asp Leu Pro Ile Ala Leu Leu Ile Ala Leu Gln Lys Gln Glu Leu Ala
            85                  90                  95

Phe Lys Glu Trp Phe Ala Phe Gly Glu Leu Gly Leu Asp Gly Lys Ile
            100                 105                 110

Lys Pro Asn Pro Asn Ile Phe Pro Met Leu Leu Asp Ile Ala Ile Lys
            115                 120                 125

His Pro His Ala Lys Val Ile Ala Pro Lys Ala Asn Glu Glu Leu Phe
            130                 135                 140

Ser Leu Ile Pro Asn Leu Gln Cys Phe Phe Val Glu His Phe Lys Glu
145                 150                 155                 160
```

Ala Leu Glu Ile Leu Gln Asn Pro Gly Ile Lys Ala Asp Thr His Thr
                165                 170                 175

Lys Lys Leu Pro Phe Lys Thr Ile Glu Leu Asn Asp Lys Glu Tyr Tyr
            180                 185                 190

Phe Ser Asp Ala Tyr Ala Leu Asp Phe Lys Glu Val Lys Gly Gln Ala
        195                 200                 205

Val Ala Lys Glu Ala Ala Leu Ile Ala Ser Ala Gly Phe His Asn Leu
    210                 215                 220

Ile Leu Glu Gly Ser Pro Gly Cys Gly Lys Ser Met Ile Ile Asn Arg
225                 230                 235                 240

Met Arg Tyr Ile Leu Pro Pro Leu Ser Leu Asn Glu Ile Leu Glu Ala
                245                 250                 255

Thr Lys Leu Arg Ile Leu Ser Glu Gln Asp Ser Ala Tyr Tyr Pro Leu
            260                 265                 270

Arg Ser Phe Arg Asn Pro His Gln Ser Ala Ser Lys Ser Ser Ile Leu
        275                 280                 285

Gly Ser Ser Ser Leu Lys Glu Pro Lys Pro Gly Glu Ile Ala Val Ala
    290                 295                 300

His Asn Gly Met Leu Phe Phe Asp Glu Leu Pro His Phe Lys Lys Glu
305                 310                 315                 320

Ile Leu Glu Ala Leu Arg Glu Pro Leu Glu Asn Asn Lys Leu Val Val
                325                 330                 335

Ser Arg Val His Ser Lys Ile Glu Tyr Glu Thr Ser Phe Leu Phe Val
            340                 345                 350

Gly Ala Gln Asn Pro Cys Leu Cys Gly Asn Leu Leu Ser Ala Thr Lys
        355                 360                 365

Ala Cys Arg Cys Gln Asp Arg Glu Ile Thr Gln Tyr Lys Asn Arg Leu
    370                 375                 380

Ser Glu Pro Phe Leu Asp Arg Ile Asp Leu Phe Val Gln Met Glu Glu
385                 390                 395                 400

Gly Asn Tyr Lys Asp Thr Pro Ser His Ser Trp Thr Ser Lys Glu Met
                405                 410                 415

His Gln Leu Val Leu Leu Ala Phe Lys Gln Lys Leu Arg Lys Gln
            420                 425                 430

Ser Val Phe Asn Gly Lys Leu Asn Glu Glu Gln Ile Glu Arg Phe Cys
        435                 440                 445

Pro Leu Asn Ala Glu Ala Lys Lys Leu Leu Glu Gln Ala Val Glu Arg
    450                 455                 460

Phe Asn Leu Ser Met Arg Ser Val Asn Lys Val Lys Val Ala Arg
465                 470                 475                 480

Thr Ile Ala Asp Leu Asn Ala Cys Glu Asn Ile Glu Lys Ser His Met
                485                 490                 495

Leu Lys Ala Leu Ser Phe Arg Lys Ile Ser
            500                 505

(2) INFORMATION FOR SEQ ID NO: 6:

(i) SEQUENCE CHARACTERISTICS:
        (A) LENGTH: 309 amino acids
        (B) TYPE: amino acid
        (C) STRANDEDNESS:
        (D) TOPOLOGY: linear (ii) MOLECULE TYPE: protein (iii) HYPOTHETICAL: YES (v) FRAGMENT TYPE: C-terminal (vi) ORIGINAL SOURCE:
    (A) ORGANISM: Helicobacter pylori
    (B) STRAIN: Helicobacter pylori 69A
    (C) INDIVIDUAL ISOLATE: Clinical isolate 69A (vii) IMMEDIATE SOURCE:
    (A) LIBRARY: Helicobacter 69A - gene library in vector
        pRH160
    (B) CLONE: pRH948

(xi) SEQUENCE DESCRIPTION: SEQ ID NO: 6:

```
Asp Pro Ala Leu Met Arg Pro Gly Arg Phe Asp Arg Gln Val Leu Val
 1               5                  10                  15

Asp Lys Pro Asp Phe Asn Gly Arg Val Glu Ile Leu Lys Val His Ile
             20                  25                  30

Lys Gly Val Lys Leu Ala Asn Asp Val Asn Leu Gln Glu Val Ala Lys
             35                  40                  45

Leu Thr Ala Gly Leu Ala Gly Ala Asp Leu Ala Asn Ile Ile Asn Glu
 50                  55                  60

Ala Ala Leu Leu Ala Gly Arg Asn Asn Gln Lys Glu Val Arg Gln Gln
65                   70                  75                  80

His Leu Lys Glu Ala Val Glu Arg Gly Ile Ala Gly Leu Glu Lys Lys
             85                  90                  95

Ser Arg Arg Ile Ser Pro Lys Glu Lys Ile Val Ala Tyr His Glu
            100                 105                 110

Ser Gly His Ala Val Ile Ser Glu Met Thr Lys Gly Ser Ala Arg Val
            115                 120                 125

Asn Lys Val Ser Ile Ile Pro Arg Gly Met Ala Ala Leu Gly Tyr Thr
130                 135                 140

Leu Asn Thr Pro Glu Glu Asn Lys Tyr Leu Met Gln Lys His Glu Leu
145                 150                 155                 160

Ile Ala Glu Ile Asp Val Leu Leu Gly Gly Arg Ala Ala Glu Asp Val
            165                 170                 175

Phe Leu Glu Glu Ile Ser Thr Gly Ala Ser Asn Asp Leu Glu Arg Ala
            180                 185                 190

Thr Asp Ile Ile Lys Gly Met Val Ser Tyr Tyr Gly Met Ser Ser Val
            195                 200                 205

Ser Gly Leu Met Val Leu Glu Lys Gln Arg Asn Ala Phe Leu Gly Gly
            210                 215                 220

Gly Tyr Gly Ser Ser Arg Glu Phe Ser Glu Lys Thr Ala Glu Glu Met
225                 230                 235                 240

Asp Leu Phe Ile Lys Asn Leu Leu Glu Glu Arg Tyr Glu His Val Lys
            245                 250                 255

Gln Thr Leu Ser Asp Tyr Arg Glu Ala Ile Glu Ile Met Val Lys Glu
            260                 265                 270

Leu Phe Asp Lys Glu Val Ile Thr Gly Glu Arg Val Arg Glu Ile Ile
            275                 280                 285

Ser Glu Tyr Glu Val Ala Asn Asn Leu Glu Ser Arg Leu Ile Pro Leu
290                 295                 300

Glu Glu Gln Ala Ser
305
```

(2) INFORMATION FOR SEQ ID NO: 7:

(i) SEQUENCE CHARACTERISTICS:
        (A) LENGTH: 237 amino acids
        (B) TYPE: amino acid
        (C) STRANDEDNESS:

(D) TOPOLOGY: linear (ii) MOLECULE TYPE: protein (iii) HYPOTHETICAL: YES (vi) ORIGINAL SOURCE:
          (A) ORGANISM: Helicobacter pylori
          (B) STRAIN: Helicobacter 69A
          (C) INDIVIDUAL ISOLATE: Clinical isolate 69A (vii) IMMEDIATE SOURCE:
          (A) LIBRARY: Helicobacter pylori 69A - gene library in
              vector pRH160
          (B) CLONE: pRH948

(xi) SEQUENCE DESCRIPTION: SEQ ID NO: 7:

Met Pro Ile Asn Pro Leu Tyr Leu Phe Pro Asn Leu Phe Thr Ala Ser
1               5                   10                  15

Ser Ile Phe Leu Gly Met Met Ser Ile Phe Tyr Ala Ser Ser Tyr Gln
            20                  25                  30

Phe Val Met Ala Cys Trp Leu Val Ala Ser Leu Ile Leu Asp Gly
        35                  40                  45

Leu Asp Gly Arg Val Ala Arg Leu Thr Asn Thr Thr Ser Lys Phe Gly
50                  55                  60

Ile Glu Phe Asp Ser Leu Ala Asp Val Ile Ala Phe Gly Val Ala Pro
65                  70                  75                  80

Ser Leu Ile Thr Tyr Phe Tyr Val Gly Tyr Asn Phe Gly Arg Ile Gly
            85                  90                  95

Met Ala Val Ser Ala Leu Phe Val Ile Phe Gly Ala Ile Arg Leu Ala
            100                 105                 110

Arg Phe Asn Ile Ser Thr Asn Thr Ser Asp Pro Tyr Ser Phe Ile Gly
            115                 120                 125

Ile Pro Ile Pro Ala Ala Ala Val Leu Val Val Leu Cys Val Leu Leu
130                 135                 140

Asp Asn Lys Tyr His Phe Leu Glu Gly Asn Thr Glu Lys Leu Phe Leu
145                 150                 155                 160

Ser Phe Ile Val Leu Leu Gly Val Leu Met Val Ser Asn Ile Arg Tyr
                165                 170                 175

Pro Asn Phe Lys Lys Val Lys Trp Asn Leu Lys Leu Phe Ile Leu Val
            180                 185                 190

Leu Ile Phe Leu Ser Leu Val Phe Val Arg Pro Leu Glu Ala Leu Ser
            195                 200                 205

Val Phe Met Gly Leu Tyr Leu Ile Tyr Gly Ile Ile Arg Trp Leu Phe
            210                 215                 220

Leu Met Val Lys Ile Ile Phe Asn Lys Asn Lys Ser Ala
225                 230                 235

(2) INFORMATION FOR SEQ ID NO: 8:

(i) SEQUENCE CHARACTERISTICS:
          (A) LENGTH: 48 amino acids
          (B) TYPE: amino acid
          (C) STRANDEDNESS:
          (D) TOPOLOGY: linear (ii) MOLECULE TYPE: protein (iii) HYPOTHETICAL: YES (vi) ORIGINAL SOURCE:
          (A) ORGANISM: Helicobacter pylori
          (B) STRAIN: Helicobacter pylori 69A
          (C) INDIVIDUAL ISOLATE: Clinical isolate 69A (vii) IMMEDIATE SOURCE:
    (A) LIBRARY: Helicobacter pylori 69A - gene library in
        vector pRH160
    (B) CLONE: pRH948

(xi) SEQUENCE DESCRIPTION: SEQ ID NO: 8:

Met Glu Ser Gln Ala Phe Tyr Leu Ser Val Asp Phe Ile Val Ser
1               5                   10                  15

Val Cys Ala Pro Phe Arg Gly Phe Lys Arg Val Tyr Gly Val Val Phe
            20                  25                  30

Asp Leu Trp His His Ser Val Ala Phe Phe Asn Gly Lys Asn Tyr Phe
            35                  40                  45

(2) INFORMATION FOR SEQ ID NO: 9:

(i) SEQUENCE CHARACTERISTICS:
        (A) LENGTH: 741 amino acids
        (B) TYPE: amino acid
        (C) STRANDEDNESS:
        (D) TOPOLOGY: linear (ii) MOLECULE TYPE: protein (iii) HYPOTHETICAL: YES (vi) ORIGINAL SOURCE:
        (A) ORGANISM: Helicobacter pylori
        (B) STRAIN: Helicobacter pylori 69A
        (C) INDIVIDUAL ISOLATE: Clinical isolate 69A (vii) IMMEDIATE SOURCE:
        (A) LIBRARY: Helicobacter pylori 69A - gene library in
            vector pRH160
        (B) CLONE: pRH948

(xi) SEQUENCE DESCRIPTION: SEQ ID NO: 9:

Met Lys Glu Ser Phe Tyr Ile Glu Gly Met Thr Cys Thr Ala Cys Ser
1               5                   10                  15

Ser Gly Ile Glu Arg Ser Leu Gly Arg Lys Ser Phe Val Lys Lys Ile
            20                  25                  30

Glu Val Ser Leu Leu Asn Lys Ser Ala Asn Ile Glu Phe Asn Glu Asn
            35                  40                  45

Glu Thr Asn Leu Asp Glu Ile Phe Lys Leu Ile Glu Lys Leu Gly Tyr
            50                  55                  60

Ser Pro Lys Lys Thr Leu Ala Glu Glu Lys Lys Glu Phe Phe Ser Pro
65                  70                  75                  80

Asn Val Lys Leu Ala Leu Ala Val Ile Phe Thr Leu Phe Val Val Tyr
                85                  90                  95

Leu Ser Met Gly Ala Met Leu Ser Pro Ser Leu Leu Pro Glu Ser Leu
                100                 105                 110

Leu Thr Ile Asn Asn His Ser Asn Phe Leu Asn Ala Cys Leu Gln Leu
            115                 120                 125

Ile Gly Thr Leu Ile Val Met His Leu Gly Arg Asp Phe Tyr Ile Gln
            130                 135                 140

Gly Phe Lys Ala Leu Trp His Arg Gln Pro Asn Met Ser Ser Leu Ile
145                 150                 155                 160

Ala Ile Gly Thr Ser Ala Ala Leu Ile Ser Ser Leu Trp Gln Leu Tyr
                165                 170                 175

Phe Val Tyr Thr Ser Gln Trp Ser Tyr Gly His Tyr Tyr Phe Glu Ser
            180                 185                 190

Val Cys Val Ile Leu Met Phe Val Met Val Gly Lys Arg Ile Glu Asn
            195                 200                 205

-continued

```
Val Ser Lys Asp Lys Ala Leu Asp Ala Met Gln Ala Leu Met Lys Asn
    210                 215                 220

Ala Pro Lys Thr Ala Leu Lys Met His Asn Asn Gln Gln Ile Glu Val
225                 230                 235                 240

Leu Val Asp Ser Ile Val Val Gly Asp Ile Leu Lys Val Leu Pro Gly
                245                 250                 255

Ser Ala Ile Ala Val Asp Gly Glu Ile Ile Glu Gly Gly Glu Leu
                260                 265                 270

Asp Glu Ser Met Leu Ser Gly Glu Ala Leu Pro Val Tyr Lys Lys Val
            275                 280                 285

Gly Asp Lys Val Phe Ser Gly Thr Phe Asn Ser His Thr Ser Phe Leu
        290                 295                 300

Met Lys Ala Thr Gln Asp Asn Lys Asn Ser Thr Leu Ser Gln Ile Val
305                 310                 315                 320

Glu Met Ile His Asn Ala Gln Ser Ser Lys Ala Glu Ile Ser Arg Leu
                325                 330                 335

Ala Asp Lys Val Ser Ser Val Phe Val Pro Ser Val Ile Ala Ile Ala
                340                 345                 350

Ile Leu Ala Phe Val Val Trp Leu Ile Ile Ala Pro Lys Pro Asp Phe
            355                 360                 365

Trp Trp Asn Phe Gly Ile Ala Leu Glu Val Phe Val Ser Val Leu Val
            370                 375                 380

Ile Ser Cys Pro Cys Ala Leu Gly Leu Ala Thr Pro Met Ser Ile Leu
385                 390                 395                 400

Val Ala Asn Gln Lys Ala Ser Ser Leu Gly Leu Phe Phe Lys Asp Ala
                405                 410                 415

Lys Ser Leu Glu Lys Ala Arg Leu Val Asn Thr Ile Val Phe Asp Lys
                420                 425                 430

Thr Gly Thr Leu Thr Asn Gly Lys Pro Val Val Lys Ser Val His Ser
            435                 440                 445

Asn Ile Glu Leu Leu Glu Leu Leu Ser Leu Ala Gly Ser Ile Glu Lys
    450                 455                 460

Ser Ser Glu His Val Ile Ala Lys Gly Ile Val Glu Tyr Ala Lys Glu
465                 470                 475                 480

His Asn Ala Pro Leu Lys Glu Met Ser Glu Val Lys Val Lys Thr Gly
                485                 490                 495

Phe Gly Ile Ser Ala Lys Thr Asp Tyr Gln Gly Ala Lys Glu Val Ile
                500                 505                 510

Lys Val Gly Asn Ser Glu Phe Phe Asn Pro Ile Asn Ala Leu Glu Ile
            515                 520                 525

Gln Glu Asn Gly Ile Leu Val Phe Val Gly Arg Val Ile Ser Glu Lys
    530                 535                 540

Glu Asp Glu Leu Leu Gly Ala Phe Val Leu Glu Asp Leu Pro Lys Lys
545                 550                 555                 560

Gly Val Lys Glu His Ile Ala Gln Ile Lys Lys Leu Gly Ile Asn Thr
                565                 570                 575

Phe Leu Leu Ser Gly Asp Asn Arg Glu Asn Val Lys Lys Cys Ala Leu
            580                 585                 590

Glu Leu Gly Ile Asp Gly Tyr Ile Ser Asn Ala Lys Pro Gln Asp Lys
            595                 600                 605

Leu Asn Lys Ile Lys Glu Leu Lys Glu Lys Gly Gln Ile Val Met Met
    610                 615                 620

Val Gly Asp Gly Leu Asn Asp Ala Pro Ser Leu Ala Met Ser Asp Val
```

```
                625                 630                 635                 640
    Ala Val Val Met Ala Lys Gly Ser Asp Val Ser Val Gln Ala Ala Asp
                        645                 650                 655

Ile Val Ser Phe Asn Asn Asp Ile Lys Ser Val Tyr Ser Ala Ile Lys
                        660                 665                 670

Leu Ser Gln Ala Thr Ile Lys Asn Ile Lys Glu Asn Leu Phe Trp Ala
                        675                 680                 685

Phe Cys Tyr Asn Ser Val Phe Ile Pro Leu Ala Cys Gly Val Leu Tyr
                        690                 695                 700

Lys Ala Asn Ile Met Leu Ser Pro Ala Ile Ala Gly Leu Ala Met Ser
    705                 710                 715                 720

Leu Ser Ser Val Ser Val Val Leu Asn Ser Gln Arg Leu Arg Asn Phe
                        725                 730                 735

Lys Ile Lys Asp His
                        740
```

(2) INFORMATION FOR SEQ ID NO: 10:

(i) SEQUENCE CHARACTERISTICS:
        (A) LENGTH: 66 amino acids
        (B) TYPE: amino acid
        (C) STRANDEDNESS:
        (D) TOPOLOGY: linear (ii) MOLECULE TYPE: protein (iii) HYPOTHETICAL: YES (vi) ORIGINAL SOURCE:
        (A) ORGANISM: Helicobacter pylori
        (B) STRAIN: Helicobacter pylori 69A
        (C) INDIVIDUAL ISOLATE: Clinical isolate 69A (vii) IMMEDIATE SOURCE:
        (A) LIBRARY: Helicobacter pylori 69A - gene library in
            vector pRH160
        (B) CLONE: pRH948

(xi) SEQUENCE DESCRIPTION: SEQ ID NO: 10:

```
Met Lys Val Thr Phe Gln Val Pro Ser Ile Thr Cys Asn His Cys Val
1               5                   10                  15

Asp Lys Ile Glu Lys Phe Val Gly Glu Ile Glu Gly Val Ser Phe Ile
                20                  25                  30

Asp Ala Ser Val Glu Lys Lys Ser Val Val Glu Phe Asp Ala Pro
                35                  40                  45

Ala Thr Gln Asp Leu Ile Lys Glu Ala Leu Leu Asp Ala Gly Gln Glu
            50                  55                  60

Val Ile
65
```

(2) INFORMATION FOR SEQ ID NO: 11:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: protein (iii) HYPOTHETICAL: YES (v) FRAGMENT TYPE: N-terminal (vi) ORIGINAL SOURCE:
        (A) ORGANISM: Helicobacter pylori (B) STRAIN: Helicobacter pylori 69A
            (C) INDIVIDUAL ISOLATE: Clinical isolate 69A (vii) IMMEDIATE SOURCE:
            (A) LIBRARY: Helicobacter pylori 69A - gene library in
                 vector pRH160
            (B) CLONE: pRH948

(xi) SEQUENCE DESCRIPTION: SEQ ID NO: 11:

Met Val Ile Tyr His Asn His Lys Arg Lys Asn Tyr Arg Ile Ser Pro
1               5                  10                  15

Phe Ser Tyr Ser Asn Phe Leu Tyr Ile Arg Ile
            20                  25

(2) INFORMATION FOR SEQ ID NO: 12:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: protein (iii) HYPOTHETICAL: YES (v) FRAGMENT TYPE: internal (ix) FEATURE:
            (A) NAME/KEY: Protein
            (B) LOCATION:1
            (D) OTHER INFORMATION:/note= "Xaa is Ile or Leu"

(xi) SEQUENCE DESCRIPTION: SEQ ID NO: 12:

Asp Lys Thr Gly Thr Xaa Thr
-5                       1

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (ix) FEATURE:
            (A) NAME/KEY: misc_feature
            (B) LOCATION:9
            (D) OTHER INFORMATION:/note= "N is C or A"

(ix) FEATURE:
            (A) NAME/KEY: misc_feature
            (B) LOCATION:15
            (D) OTHER INFORMATION:/note= "N is C or G"

(ix) FEATURE:
            (A) NAME/KEY: misc_feature
            (B) LOCATION:16
            (D) OTHER INFORMATION:/note= "N is A or T"

(ix) FEATURE:
            (A) NAME/KEY: misc_feature
            (B) LOCATION:18
            (D) OTHER INFORMATION:/note= "N is C or G"

(xi) SEQUENCE DESCRIPTION: SEQ ID NO: 13:

GATAAAACNG GCACNNTNAC                                                    20

(2) INFORMATION FOR SEQ ID NO: 14:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (ix) FEATURE:
    (A) NAME/KEY: misc_feature
    (B) LOCATION:3
    (D) OTHER INFORMATION:/note= "N is T or C"

(ix) FEATURE:
    (A) NAME/KEY: misc_feature
    (B) LOCATION:6
    (D) OTHER INFORMATION:/note= "N is A or G"

(ix) FEATURE:
    (A) NAME/KEY: misc_feature
    (B) LOCATION:9
    (D) OTHER INFORMATION:/note= "N is A, G, C or T"

(ix) FEATURE:
    (A) NAME/KEY: misc_feature
    (B) LOCATION:12
    (D) OTHER INFORMATION:/note= "N is A, G, C or T"

(ix) FEATURE:
    (A) NAME/KEY: misc_feature
    (B) LOCATION:15
    (D) OTHER INFORMATION:/note= "N is A, G, T or C"

(ix) FEATURE:
    (A) NAME/KEY: misc_feature
    (B) LOCATION:18
    (D) OTHER INFORMATION:/note= "N is T or C"

(xi) SEQUENCE DESCRIPTION: SEQ ID NO: 14:

GANAANACNG GNACNATNAC                                          20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (ix) FEATURE:
        (A) NAME/KEY: misc_feature
        (B) LOCATION:3
        (D) OTHER INFORMATION:/note= "N is T or C"

(ix) FEATURE:
        (A) NAME/KEY: misc_feature
        (B) LOCATION:6
        (D) OTHER INFORMATION:/note= "N is A or G"

(ix) FEATURE:
        (A) NAME/KEY: misc_feature
        (B) LOCATION:9
        (D) OTHER INFORMATION:/note= "N is A, G, C or T"

(ix) FEATURE:
        (A) NAME/KEY: misc_feature
        (B) LOCATION:12
        (D) OTHER INFORMATION:/note= "N is A, G, C or T"

(ix) FEATURE:
        (A) NAME/KEY: misc_feature

-continued

```
            (B) LOCATION:15
            (D) OTHER INFORMATION:/note= "N is A, G, T or C"

(ix) FEATURE:
            (A) NAME/KEY: misc_feature
            (B) LOCATION:18
            (D) OTHER INFORMATION:/note= "N is C or A"

(xi) SEQUENCE DESCRIPTION: SEQ ID NO: 15:

GANAANACNG GNACNATNAC                                                       20

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (ix) FEATURE:
            (A) NAME/KEY: misc_feature
            (B) LOCATION:3
            (D) OTHER INFORMATION:/note= "N is T or C"

(ix) FEATURE:
            (A) NAME/KEY: misc_feature
            (B) LOCATION:6
            (D) OTHER INFORMATION:/note= "N is A or G"

(ix) FEATURE:
            (A) NAME/KEY: misc_feature
            (B) LOCATION:9
            (D) OTHER INFORMATION:/note= "N is A, G, C or T"

(ix) FEATURE:
            (A) NAME/KEY: misc_feature
            (B) LOCATION:12
            (D) OTHER INFORMATION:/note= "N is A, G, C or T"

(ix) FEATURE:
            (A) NAME/KEY: misc_feature
            (B) LOCATION:15
            (D) OTHER INFORMATION:/note= "N is A, G, T or C"

(ix) FEATURE:
            (A) NAME/KEY: misc_feature
            (B) LOCATION:18
            (D) OTHER INFORMATION:/note= "N is A or G"

(xi) SEQUENCE DESCRIPTION: SEQ ID NO: 16:

GANAANACNG GNACNTTNAC                                                       20

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (ix) FEATURE:
            (A) NAME/KEY: misc_feature
            (B) LOCATION:3
            (D) OTHER INFORMATION:/note= "N is T or C"

(ix) FEATURE:
            (A) NAME/KEY: misc_feature
            (B) LOCATION:6
```

(D) OTHER INFORMATION:/note= "N is A or G"

(ix) FEATURE:
                (A) NAME/KEY: misc_feature
                (B) LOCATION:9
                (D) OTHER INFORMATION:/note= "N is A, G, C or T"

(ix) FEATURE:
                (A) NAME/KEY: misc_feature
                (B) LOCATION:12
                (D) OTHER INFORMATION:/note= "N is A, G, C or T"

(ix) FEATURE:
                (A) NAME/KEY: misc_feature
                (B) LOCATION:15
                (D) OTHER INFORMATION:/note= "N is A, G, T or C"

(ix) FEATURE:
                (A) NAME/KEY: misc_feature
                (B) LOCATION:18
                (D) OTHER INFORMATION:/note= "N is T or C"

(xi) SEQUENCE DESCRIPTION: SEQ ID NO: 17:

GANAANACNG GNACNCTNAC                                                    20

(2) INFORMATION FOR SEQ ID NO: 18:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid (iii) HYPOTHETICAL: NO (ix) FEATURE:
                (A) NAME/KEY: misc_feature
                (B) LOCATION:3
                (D) OTHER INFORMATION:/note= "N is T or C"

(ix) FEATURE:
                (A) NAME/KEY: misc_feature
                (B) LOCATION:6
                (D) OTHER INFORMATION:/note= "N is A or G"

(ix) FEATURE:
                (A) NAME/KEY: misc_feature
                (B) LOCATION:9
                (D) OTHER INFORMATION:/note= "N is A, G, C or T"

(ix) FEATURE:
                (A) NAME/KEY: misc_feature
                (B) LOCATION:12
                (D) OTHER INFORMATION:/note= "N is A, G, C or T"

(ix) FEATURE:
                (A) NAME/KEY: misc_feature
                (B) LOCATION:15
                (D) OTHER INFORMATION:/note= "N is A, G, T or C"

(ix) FEATURE:
                (A) NAME/KEY: misc_feature
                (B) LOCATION:18
                (D) OTHER INFORMATION:/note= "N is A or G"

(xi) SEQUENCE DESCRIPTION: SEQ ID NO: 18:

GANAANACNG GNACNCTNAC                                                    20

(2) INFORMATION FOR SEQ ID NO: 19:

(i) SEQUENCE CHARACTERISTICS:
                (A) LENGTH: 10 amino acids
                (B) TYPE: amino acid
                (C) STRANDEDNESS:

```
        (D) TOPOLOGY: linear (ii) MOLECULE TYPE: peptide (iii) HYPOTHETICAL: YES (v) FRAGMENT TYPE: internal (xi) SEQUENCE DESCRIPTION: SEQ ID NO: 19:

His Ile His Asn Leu Asp Cys Pro Asp Cys
1               5                   10

(2) INFORMATION FOR SEQ ID NO: 20:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO: 20:

Gly Ser Pro Gly Cys Gly Lys Ser
1               5

(2) INFORMATION FOR SEQ ID NO: 21:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: protein (iii) HYPOTHETICAL: YES (v) FRAGMENT TYPE: internal (vi) ORIGINAL SOURCE:
         (A) ORGANISM: Helicobacter pylori
         (B) STRAIN: Helicobacter pylori 69A
         (C) INDIVIDUAL ISOLATE: Clinical isolate 69A (vii) IMMEDIATE SOURCE:
         (A) LIBRARY: Helicobacter pylori 69A - gene library in
             vector pRH160
         (B) CLONE: pRH948

(xi) SEQUENCE DESCRIPTION: SEQ ID NO: 21:

Cys Xaa Xaa Cys
1

(2) INFORMATION FOR SEQ ID NO: 22:

(i) SEQUENCE CHARACTERISTICS:
         (A) LENGTH: 52 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "(MCS1) Multi Cloning Site 1"

(iii) HYPOTHETICAL: NO (xi) SEQUENCE DESCRIPTION: SEQ ID NO: 22:

GAATTCGTAG GAAGCTCATA TGGTCGACTC TAGACCCGGG CTGCAGAAGC TT          52
```

(2) INFORMATION FOR SEQ ID NO: 23:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "DNA Primer"

(iii) HYPOTHETICAL: NO (xi) SEQUENCE DESCRIPTION: SEQ ID NO: 23:

ACCGACTTGA ATTCATGCAA GAATACCACA TT                              32

(2) INFORMATION FOR SEQ ID NO: 24:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "DNA Primer"

(xi) SEQUENCE DESCRIPTION: SEQ ID NO: 24:

CTGCAACTCA AGCTTAAGCT CTCATTGCGC GCAT                            34